US010473566B2

United States Patent
Laugharn, Jr. et al.

(10) Patent No.: US 10,473,566 B2
(45) Date of Patent: Nov. 12, 2019

(54) BLOOD SAMPLING, STORAGE AND TREATMENT APPARATUS

(71) Applicant: Covaris, Inc., Woburn, MA (US)

(72) Inventors: James A. Laugharn, Jr., Boston, MA (US); Hans-Ulrich Thomann, Stow, MA (US)

(73) Assignee: Covaris, Inc., Woburn, MA (US)

( * ) Notice: Subject to any disclaimer, the term of this patent is extended or adjusted under 35 U.S.C. 154(b) by 310 days.

(21) Appl. No.: 15/287,828

(22) Filed: Oct. 7, 2016

(65) Prior Publication Data

US 2017/0102299 A1 Apr. 13, 2017

Related U.S. Application Data

(60) Provisional application No. 62/238,786, filed on Oct. 8, 2015.

(51) Int. Cl.
| | | |
|---|---|---|
| *G01N 1/40* | (2006.01) | |
| *B01L 3/00* | (2006.01) | |
| *A61B 5/15* | (2006.01) | |

(52) U.S. Cl.
CPC ......... *G01N 1/40* (2013.01); *A61B 5/150351* (2013.01); *A61B 5/150755* (2013.01); *B01L 3/5082* (2013.01); *B01L 3/50825* (2013.01); *G01N 1/405* (2013.01); *B01L 3/502* (2013.01); *B01L 2200/185* (2013.01); *B01L 2300/021* (2013.01); *B01L 2300/042* (2013.01); *B01L 2300/046* (2013.01); *B01L 2300/047* (2013.01); *B01L 2300/069* (2013.01); *B01L 2300/0832* (2013.01); *B01L 2300/105* (2013.01); *B01L 2300/12* (2013.01)

(58) Field of Classification Search
CPC .... G01N 1/40; G01N 1/405; A61B 5/150351; A61B 5/150755; B01L 3/5082; B01L 3/50825; B01L 2300/12; B01L 2300/021; B01L 2300/0832; B01L 2300/046; B01L 2300/042; B01L 2200/185; B01L 2300/105; B01L 3/502; B01L 2300/047; B01L 2300/069
See application file for complete search history.

(56) References Cited

U.S. PATENT DOCUMENTS

| | | |
|---|---|---|
| 4,883,764 A | 11/1989 | Kloepfer |
| 5,266,219 A | 11/1993 | Pall et al. |
| 2004/0267181 A1 | 12/2004 | Tuite et al. |

(Continued)

FOREIGN PATENT DOCUMENTS

| | | |
|---|---|---|
| EP | 2 168 975 A2 | 3/2010 |
| EP | 2 785 859 A1 | 10/2014 |

OTHER PUBLICATIONS

International Search Report and Written Opinion for Application No. PCT/US2016/055900, dated Jan. 2, 2017.

*Primary Examiner* — Sally A Merkling
(74) *Attorney, Agent, or Firm* — Wolf, Greenfield & Sacks, P.C.

(57) ABSTRACT

Systems and methods for collecting blood and other liquid samples. A sample holder may include a cap and porous element arranged to receive a blood or other liquid sample. The porous element may be stored in a sealed container, e.g., immediately after blood sample collection, and the sample dried while sealed in the container.

13 Claims, 14 Drawing Sheets

(56) References Cited

U.S. PATENT DOCUMENTS

| | | | |
|---|---|---|---|
| 2009/0197283 A1* | 8/2009 | Gold | B01L 3/5029 435/7.9 |
| 2013/0116597 A1* | 5/2013 | Rudge | A61B 5/150358 600/575 |
| 2014/0141411 A1* | 5/2014 | Lloyd, Jr. | B01L 3/50825 435/5 |
| 2014/0295429 A1 | 10/2014 | Hogan et al. | |

* cited by examiner

BLOOD SAMPLING, STORAGE AND TREATMENT APPARATUS

CROSS REFERENCE TO RELATED APPLICATION

This application claims the benefit of U.S. Provisional Application No. 62/238,786, filed Oct. 8, 2015, which is hereby incorporated by reference in its entirety.

BACKGROUND

1. Field of the Invention

Systems and methods for collecting, storing and treating biological samples such as blood are generally disclosed.

2. Related Art

Dried blood spots provide for a method of biosampling where fresh blood samples taken from a patient are blotted on to a substrate (e.g., Guthrie card, filter paper) and dried for future processing and/or analysis (e.g., disease screening). For example, the dried blood spots can be archived for long-term storage at room temperature and, at a later time, may serve as a source of biomolecules such as nucleic acids, proteins, lipids, or metabolites for further analysis by methods such as DNA sequencing, PCR, immunoassays, or high performance liquid chromatography.

SUMMARY

The inventors have appreciated that standard dried blood sampling techniques have significant drawbacks, including potential cross-contamination, mislabeling of a sample, unsuitable drying of the blood sample and/or exposure of a blood sample to relatively high humidity or other environmental conditions during storage that can harm the sample. Cross-contamination can occur because a blood sample taken from a patient, e.g., by a capillary tube or directly transferred to a paper or other substrate that is exposed to environmental contaminants before, during and/or after transfer of the blood sample to the substrate. For example, the paper or other substrate used to receive the blood sample is handled by a person in preparation for accepting the sample, possibly being placed on a table top or other surface so blood can be spotted onto the substrate. Such handling can expose the substrate to contaminants, whether airborne, dropped onto the substrate, and so on. Also, after the blood sample is placed onto the substrate, the sample must be dried prior to storage. Drying often occurs in an exposed environment, e.g., by manually waving the substrate in air, which can further expose the sample to potential contamination. Also, variable humidity, temperature and other environmental factors can cause different samples to be dried to different degrees and in different ways. These variations can affect the quality of the sample and results from obtained in later analysis of the sample. Finally, analysis of the dried blood sample typically requires that the sample be separated from the main substrate body, e.g., by cutting or punching a section of a card that holds the sample from the main body of the card. This operation can again expose the sample to potential contamination, e.g., from the cutting device, as well as risk mislabeling of the sample because the sample is separated from the substrate and no longer has an associated identifier. That is, while a blood card may include identifying indicia, such as a patient name, once the blood spot is punched from the card, the blood spot is separated from identifying indicia, which can lead to mislabeling or improper tracking of the sample.

Aspects of the invention provide a method and apparatus to help reduce potential contamination and/or improve drying or storage conditions for a blood sample, including a blood sample that is stored in a dried form. Aspects of the invention may also aid in properly labeling or tracking a sample, e.g., so that the sample can be properly associated with the subject from which the sample was taken through the entire process of sample collection, storage and analysis. Aspects of the invention may also aid in transferring a dried blood sample to a treatment vessel, e.g., for recovery of biomolecules or other components of the sample.

In some embodiments, a sample holder may include a cap and a porous element attached to the cap. For example, the porous element can be glued or otherwise permanently attached to the cap, or push/pressure fitted as to allow it to be pushed out and ejected into a processing vessel, etc. The cap may include a gripping surface to allow a user to manipulate the cap and porous element. The porous element may be arranged to receive a liquid blood sample, e.g., by contacting a distal end or other portion of the porous element to liquid blood so that the blood is wicked into the porous element, or by pipetting liquid blood into an inner space of the porous element. For example, the porous element may be arranged as a cage with an inner space to hold a wet or liquid blood sample. Openings of the cage may be arranged to hold the liquid sample by surface tension, i.e., the liquid is prevented from passing through the cage openings by surface tension. Optionally, the cage may have a hydrophobic outer portion and hydrophilic inner portion that cooperate to hold a liquid sample in the inner space of the cage. In such an arrangement, the blood sample may be pipetted directly into the inner space of the cage, e.g., through an opening in the cage or through an opening (e.g., of a septum) in the cap. In other arrangements, the porous element may be arranged to wick a blood sample into an inner space of the porous element, e.g., by capillary action. In some cases, a distal end of the porous element may contact a blood sample so that the blood is wicked into the porous element. The porous element can have stabilizing agents such as EDTA, surfactants, cross-linking agents (such as formaldehyde), coagulation inducers (such as Calcium ions), etc. embedded in it. The stabilizing agent in the porous element might differ based on the biomolecule of interest to be extracted from the porous element.

Thus, the blood sample may be received into the porous element without requiring a user to physically touch the porous element. The porous element can be designed to have a wide range of fixed collection volume ranging from 1 microliter to several hundred microliters based on the sample requirements of the application for the extraction of biomolecule of interest. Once the blood sample is received by the porous element, the porous element may be placed into an internal space of a container and the blood sample allowed to dry while in the container. The internal space of the container may be sealed from an exterior environment yet be arranged to dry the blood sample inside. Thus, there may be no need to expose the sample to air for any extended period to dry the sample. In some embodiments, the container may include a desiccant or other material to receive moisture from the blood sample, allowing the sample to dry. Such an arrangement may provide a relatively controlled environment for drying of the sample, e.g., a humidity level in the space where the blood sample dries may be within a known or controlled range, helping to ensure that the blood sample dries at a desired rate and to a desired level. Also, since the blood sample may dry in an enclosed environment, such as an environment that is sealed closed, the sample may be isolated from at least some outside conditions such as humidity.

In some embodiments, the sample holder may additionally include a blotter element attached to the porous element. The blotter element may be arranged to directly contact a pool of blood, such as on a lanced fingertip, and wick blood into the blotter element. Blood serum and other blood-borne materials may be wicked from the blotter element and to the porous element so that the porous element receives a blood sample. The blood sample received by the porous element may include only blood serum and other blood-borne materials having a size smaller than a threshold, whereas the blotter element may be arranged to retain whole blood cells and other blood-borne materials having a size greater than threshold. Thus, the blotter element may function as a kind of filter for the porous element, e.g., so that the porous element can be used to extract relatively small molecules from the blood sample, and the blotter element used to extract other materials, such as DNA and other nucleic acid materials.

In some embodiments, the cap of the sample holder may be arranged to engage with a treatment vessel used to analyze a blood sample so that the porous element and an associated blood sample, which may be dried, can be received into the vessel. The cap may engage the vessel so that the porous element and sample are sealed within a volume of the vessel. In some cases, a blotter element (if used) may be separated from the porous element prior to the porous element being received in the vessel, e.g., by centrifugation, physically pulling the blotter element from the porous element, etc. A liquid material, such as a reagent used to recover biomolecules or other components of the sample, may be placed in the vessel as well, and the sample and liquid material may be treated with acoustic energy to allow recovery of the biomolecules or other materials. As a result, the blood sample may be transferred from storage and positioned in a treatment vessel without requiring direct physical handling or manipulation of the porous element, e.g., no cutting or other operation on the porous element is needed to allow for treatment to recover materials from the sample. However, in some embodiments, the porous element may be separable from the cap.

In some embodiments, the cap may include identification indicia to allow the cap/porous element, and an associated blood sample, to be uniquely identified from others. The indicia may be in the form of alphanumeric text, a barcode, RFID tag, etc., and may be attached to the cap so that the indicia and cap/porous element are associated with each other before, during and after sample collection, as well as before, during and after the sample is processed for analysis purposes. This may allow for more accurate and reliable tracking of a sample, e.g., so the sample can be properly associated with a subject from which the sample is taken. For example, at the time of taking a sample, if the indicia on the cap of a sample holder is accurately associated with a subject, the sample may be taken and one can be certain that the sample attached to the indicia was taken from the subject. This is because the sample, once received by the porous element, is physically attached to the indicia throughout sample handling, drying, and analysis steps. Such sample/indicia association is not possible with typical blood card sampling, e.g., because the portion of the blood card must be cut from the larger portion of the card to allow for analysis.

Aspects of the invention also relate to methods and apparatuses for processing biological samples such as dried blood samples with focused acoustic energy. In various embodiments, a sample including blood dried on to a substrate, such as a paper substrate, may be placed in a vessel and subjected to focused acoustic energy applied in accordance with suitable parameters and with the appropriate extraction buffers, resulting in the extraction and recovery of biomolecules from the blood in an efficient and effective manner.

For example, focused acoustical methods in accordance with the present disclosure may allow for the recovery of significantly higher yields of target biomolecules from blood samples in comparison to conventional extraction methods that do not employ such methods. Such yields may be obtained using relatively short focused acoustic treatment times (e.g., as low as approximately 10 seconds to 5 minutes in duration). In some cases, the maximum theoretical yield of DNA from a microliter of blood is 26-66 ng, calculated by multiplying the mass present in a diploid cell (6.6 pg) with the number of white blood cells present in 1 microliter (4,000 to 10,000). In some embodiments, at least 20.0 nanograms of nucleic acid (e.g., DNA, RNA) may be extracted and recovered per an amount of dried blood corresponding to approximately 5 microliters of fresh blood, i.e., a recovery rate of at least 4 nanograms/microliter fresh blood equivalent may be achieved. (A fresh blood equivalent in this context is an amount of dried blood that was collected from a specific volume of fresh blood. For example, a dried blood sample formed from 5 microliters of fresh blood is a fresh blood equivalent of 5 microliters.) In some embodiments, as discussed further below, nucleic acid may be extracted and recovered at a rate of 20.0 ng or more (e.g., up to 70.0 ng, up to 80.0 ng, up to 90.0 ng, up to 100.0 ng, up to 150.0 ng, or more) per an amount of dried blood corresponding to approximately 5 microliters of fresh blood, i.e., rates of 4, 14, 16, 18, 20 or 30 nanograms/microliter or more. Hence, for greater volumes of blood, even more nucleic acid may be extracted and recovered. Since DNA is contained within these cells the range of extracted DNA can also vary from patient to patient. This is in contrast to conventional methods where for dried blood corresponding to approximately 5 microliters of fresh blood, the maximum recovery of nucleic acid has been observed to be less than 20.0 ng. The DNA source can be from WBC, virus, bacteria, fungi, and/or parasites in the blood.

In addition, systems and methods described herein may allow for a greater amount of protein recovery relative to conventional protein extraction. In various embodiments, also described in more detail below, proteins may be extracted and recovered at a rate of 8.0 mg or more (e.g., up to 10.0 mg, up to 12.0 mg, up to 15.0 mg, or more) per an amount of dried blood corresponding to approximately 5 microliters of fresh blood, i.e., a rate of at least 1.6 milligrams/microliter fresh blood equivalent may be achieved. The theoretical total protein in a milliliter of blood can be as high as 300 mg/mL. (Schneditz et al. 1989. J. Clin. Chem. Clin. Biochem. Vol. 27, pp. 803-806). And similar to that discussed above with respect to nucleic acids, for greater volumes of blood, even more protein may be extracted and recovered. In contrast, conventional methods may yield a protein recovery of less than 8.0 mg for dried blood corresponding to approximately 5 microliters of fresh blood.

Methods of extracting biomolecules from dried blood samples that employ focused acoustics described herein may also result in significantly higher sample quality than those possible using conventional extraction methods. Such high quality of extracted biomolecules may provide for a comparatively greater amount of DNA that is amplifiable, for example, via polymerase chain reaction (PCR) and/or next generation sequencing (NGS), or otherwise useable, for example, cloning, restriction enzyme mapping, hybridization experiments etc. In some embodiments, extraction of biomolecules from blood using focused acoustics may result in a greater percentage of nucleic acid extracted from a sample via the focused acoustic energy being capable of amplification via polymerase chain reaction than nucleic acid extracted from an identical sample using extraction protocol from a QIAamp DNA Mini Kit without the focused acoustic energy. In some embodiments, at least 60% of the nucleic acid (e.g., DNA) of the extracted biomolecules recovered using focused acoustical methods in accordance with the present disclosure is capable of amplification via polymerase chain reaction (e.g., quantitative PCR). For example, through exposure of the dried blood sample to a suitable amount of focused acoustic energy, up to 80%, 90%, 95%, or 100% of the recovered DNA from the extracted biomolecules may be capable of such amplification. On the other hand, less than 50% of nucleic acid extracted and recovered using conventional methods may be capable of amplification through PCR.

In certain embodiments, at least 20.0 nanograms (e.g., greater than 50.0 ng, up to 70.0 ng, up to 80.0 ng, up to 90.0 ng, up to 100.0 ng, up to 150.0 ng, or more) of nucleic acid extracted from a dried blood sample may be capable of amplification via polymerase chain reaction per an amount of dried blood corresponding to approximately 5 microliters of fresh blood. In other words, amplifiable nucleic acid may be extracted from a dried blood sample at a rate of 20 ng or more per an amount of dried blood corresponding to 5 microliters of fresh liquid blood. And more amplifiable nucleic acid may be extracted from a blood sample having a greater volume. By contrast, less than 20.0 ng of the nucleic acid extracted and recovered from a comparable sample using conventional methods per an amount of dried blood corresponding to 5 microliters of fresh liquid blood may be capable of such amplification.

In addition to a greater level of overall recovery yield and quality of target biomolecules, focused acoustical methods of the present disclosure further allow for the DNA fragment size to be tuned as desired during the extraction. For example, fragment size resulting from acoustic treatment may vary based on treatment time. Thus, by adjusting treatment time, DNA fragment size of the extracted DNA may be adjusted. Such tuning of fragment size may be particularly suitable for analytical and/or diagnostic methods, for example, the use of NGS for disease screening.

In an illustrative embodiment, a method of processing a dried blood sample is provided. The method may include placing a sample in a vessel, the sample including blood dried on a substrate. The method may further include transmitting focused acoustic energy through a wall of the vessel such that the blood and the substrate are exposed to acoustic energy having a frequency of between about 100 kilohertz and about 100 megahertz at a focal zone having a size dimension of less than about 2 centimeters, resulting in extraction of biomolecules from the blood, wherein at least 60% of nucleic acid of the extracted biomolecules is capable of amplification via polymerase chain reaction.

In another illustrative embodiment, a method of processing a dried blood sample is provided. The method may include placing a sample in a vessel, the sample including dried blood on a substrate. The method may include transmitting focused acoustic energy through a wall of the vessel such that the blood and the substrate are exposed to acoustic energy having a frequency of between about 100 kilohertz and about 100 megahertz at a focal zone having a size dimension of less than about 2 centimeters, resulting in extraction of biomolecules from the blood. The method may further include recovering from the extracted biomolecules at least 20.0 nanograms of nucleic acid per an amount of dried blood corresponding to 5 microliters of fresh blood. Or, the method may include recovering from the extracted biomolecules at least 8.0 milligrams of protein per an amount of dried blood corresponding to 5 microliters of fresh blood.

In another illustrative embodiment, a method of processing a dried blood sample is provided. The method includes placing a sample in a vessel, the sample including blood dried on to a substrate. The method further includes transmitting focused acoustic energy through a wall of the vessel such that the blood and the substrate are exposed to acoustic energy having a frequency of between about 100 kilohertz and about 100 megahertz at a focal zone having a size dimension of less than about 2 centimeters, resulting in extraction of biomolecules from the blood, wherein a greater percentage of nucleic acid extracted from the sample via the focused acoustic energy is capable of amplification via polymerase chain reaction than nucleic acid extracted from an identical sample using extraction protocol from a QIAamp DNA Mini Kit without the focused acoustic energy.

Acoustic energy may be used to treat a sample for a variety of purposes and in a variety of ways. For example, the acoustic energy directed to the sample may be sufficient to cause at least one of cell lysing, compound extraction, permeabilizing, stirring, catalyzing, degrading, fluidization, heating, particle breakdown, separation, extraction of biomolecules (e.g., DNA, RNA, protein, etc.), from either individual porous elements, or serially from the same porous element by sequential extraction using different reagents, DNA shearing, and/or disruption of molecular bonds in the sample. The acoustic energy source may be spaced from and exterior to the vessel, and the acoustic energy may have a frequency of between about 100 kilohertz and about 100 megahertz and a focal zone having a width of less than about 2 centimeters.

Generally speaking, when aiming to recover nucleic acid, an enzyme such as Proteinase K or other enzymes, which may be used to digest protein and remove other contamination from formulations containing nucleic acid, may be added to the mixture within the vessel. An appropriate lysis buffer may also be added at a suitable time to break down cell walls or other barriers to recovery of the target biomolecule(s). The sample may then be treated with an appropriate amount of focused acoustic energy to extract and/or further process the biomolecules, as discussed further below.

Other advantages and novel features of the present disclosure will become apparent from the following detailed description of various non-limiting embodiments when considered in conjunction with the accompanying figures and claims. For example, while the extraction of certain types of biomolecules is discussed herein, a variety of different compounds may be recovered from a blood sample, including metabolites and/or other compounds included in blood.

BRIEF DESCRIPTION OF THE DRAWINGS

Aspects of the present disclosure are described with reference to the following drawings in which numerals reference like elements, and wherein.

DETAILED DESCRIPTION

Figure 1:
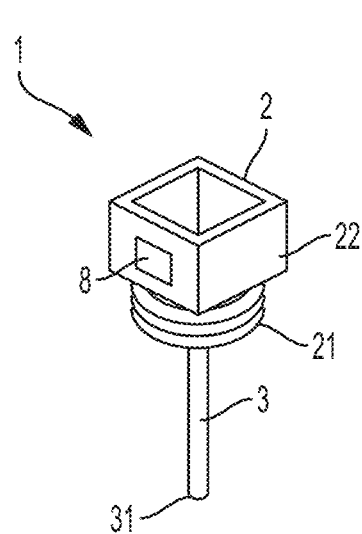
FIG. 1 shows a perspective view of a sample holder including a cap and porous element in an illustrative embodiment.

Aspects of the present disclosure are not limited in application to the details of construction and the arrangement of components set forth in the following description or illustrated in the drawings. Other embodiments may be employed and aspects of the present disclosure may be practiced or be carried out in various ways. Also, the phraseology and terminology used herein is for the purpose of description and should not be regarded as limiting.

FIG. 1 shows an illustrative embodiment of a sample holder 1 that includes a cap 2 and porous element 3 to receive a liquid blood sample and form a dried blood sample. In this embodiment, the cap 2 includes a top, a bottom, and a gripping surface 22 between the top and bottom. The gripping surface 22 may allow a user to manipulate the cap 2 and porous element 3, e.g., to position a distal end 31 or other portion of the porous element 3 in contact with liquid blood so the blood can be wicked into the porous element 3. The porous element 3, which may include a rod-shaped element made of a polymer material that includes one or more capillaries, pores or other structures to wick blood, may be attached to the bottom of the cap at a proximal end of the porous element 3 so that the porous element extends away from the cap 2. The porous element may include any suitable material, for example, cellulose, biological material and/or a synthetic polymer such as polyethylene, polypropylene, polytetrafluoroethylene, polyethylene terephthalate, or combinations thereof. The porous material may be fibrous in construction and may, for example, have a porosity and/or average pore size that is suitable for wicking and/or absorbing blood into an inner space of the porous element 3. The porous element 3 may be permanently attached or fixed to the cap 2, e.g., by adhesive, mechanical crimping or other attachment, etc., or may be removably attached to the cap, e.g., so that the porous element 3 can be separated from the cap 2 for analysis processing of the porous element 3 and associated sample. For example, the porous element 3 may have a rod-shape and a proximal end of the porous element 3 may be inserted into a receiving hole of the cap 2. The porous element 3 may be adhered, crimped, or otherwise fixed in place, or the porous element 3 may be attached by a friction fit or other arrangement that allows the porous element 3 to be separated from the cap 2. In one embodiment, the porous element 3 may be separated from the cap 2 by inserting a push rod into the receiving hole of the cap 2 and pushing the porous element distally away from the cap 2 and from the receiving hole.

In this embodiment, the cap includes an engagement feature 21, such as a screw thread, bayonet connector, locking tab, o-ring or other frictional element, arranged to engage with a vessel (not shown) so that the porous element 3 may be positioned in the vessel. The cap 2 may also include identification indicia 8, such as a barcode, alphanumeric text, RFID tag, or other element that allows for automated or manual reading of the indicia 8 so the cap 2 and porous element 3 can be uniquely identified in relation to other cap/porous element assemblies. The indicia 8 may be present on the cap 2 before the time that a blood or other sample is received by the porous element 3, or may be attached to the cap 2 after the sample is received. However, by having the indicia 8 on the cap 2 prior to reception of the sample by the porous element 3, proper association and tracking of the sample can be enhanced. That is, by having the indicia 8 automatically associated with the sample when it is received, the risk of having the sample separated from the indicia 8 at any time after reception is reduced. As a result, the indicia 8 can be associated with a subject from which a sample is taken, and one can be certain that the indicia, sample and subject are properly associated throughout handling, storage and analysis processing of the sample.

Figure 2:
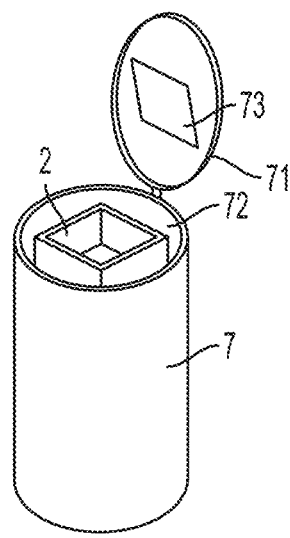
FIG. 2 shows a perspective view of a sample holder having a cap and porous element positioned in a container.

In accordance with one aspect of the invention, a blood sample can be dried after reception by the porous element 3 in an enclosed space of a container. Such an arrangement may help prevent contamination of the sample and/or help control humidity or other conditions in which the sample is dried. For example, FIG. 2 shows a container 7 of a sample holder 1 that has an internal space 72 in which a cap 2 and porous element 3 (not visible in FIG. 2) can be received. Though not shown, the container 7 may include a shelf or other support arranged to engage the cap 2 so that the porous element 3 is suspended within the internal space 72 so as to avoid contact with the walls of the container 7. This may help avoid contamination and/or aid in drying of the sample. The container 7 may have a cover 71 that can be used to close an opening to the internal space 72. With the cover 71 in the closed position (not shown—FIG. 2 shows the cover 71 in an open position), the cap 2, porous element 3 and sample may be enclosed in the internal space 72. In some embodiments, the cap, porous element and sample may be sealed from the external environment in the internal space 72, e.g., so that humidity and other conditions outside of the internal space 72 have a reduced influence on the sample. In some embodiments, the container 7 may include a desiccant 73 or other material or system to receive moisture from the sample. Thus, a freshly-taken sample may be enclosed in a sealed internal space 72 of a container 7 so that the sample can dry inside the internal space 72 in controlled conditions, such as a controlled humidity environment. This may help dry the sample at a desired rate and/or to a desired moisture level, which may aid in sample storage and/or analysis.

Although in the embodiment of FIG. 2, the cap 2 is contained within the internal space 72 with the porous element 3, the cap 2 may be located outside of the internal space 72. For example, the cap 2 may function as the cover for the container 7 so as to enclose the porous element 3 in the internal space 72. This may allow the indicia 8 to be readable while the porous element 3 is located in the internal space. In embodiments in which the cap is located in the internal space, the container 7 may have a window to allow reading of the indicia (if needed), or the container 7 may bear indicia that corresponds to the indicia 8 on the cap 2.

Figure 3:
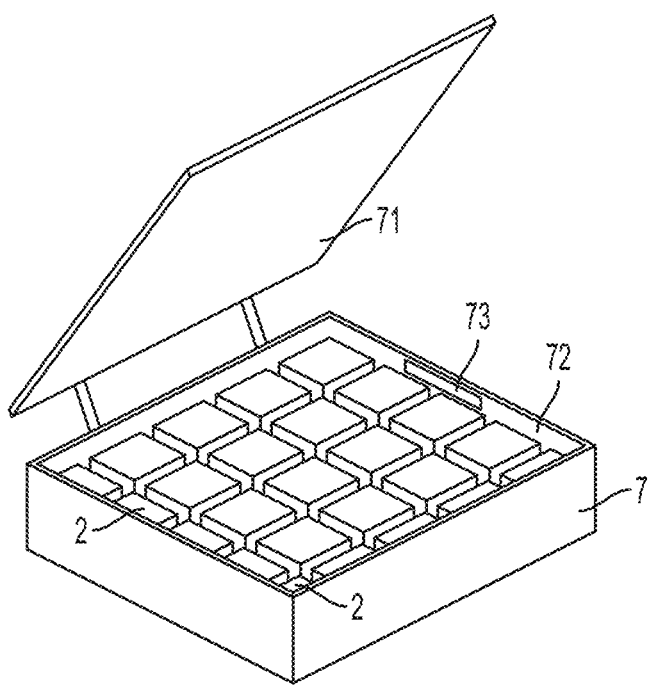
FIG. 3 shows a perspective view of a container arranged to hold a plurality of cap and porous element assemblies.

Although the container in FIG. 2 is arranged to hold only one cap/porous element assembly, the container may be arranged to hold two or more such assemblies, e.g., as shown in FIG. 3. Similar to FIG. 2, the container 7 of FIG. 3 may enclose cap/porous element assemblies (along with associated blood samples) in an enclosed internal space 72. The container 7 may have a desiccant 73 or other arrangement to receive or remove moisture from samples in the container 7. As in FIG. 2, a cover 71 may be moved between an open position shown in FIG. 2 to a closed position to enclose the cap/porous element assemblies. Alternately, the caps 2 of each cap/porous element assembly may function as a cover for the container 7, e.g., the caps 2 may engage at openings of a wall of the container 7 so as to hold the porous element 3 in the internal space.

Figure 4:
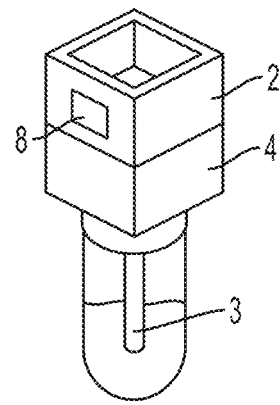
FIG. 4 shows a sample holder of FIG. 1 engaged with a vessel that contains the porous element.

As described above, the cap 2 of a sample holder 1 may be arranged to engage with one or more different vessels, whether for drying, storage and/or analysis of a sample held by the porous element 3. FIG. 4 shows an illustrative embodiment in which the engagement feature 21 of the cap 2 in the FIG. 1 embodiment is engaged with a vessel 4 such that the porous element 3 (and associated sample) is received into a volume of the vessel 4. Engagement of the cap 2 with the vessel 4 may seal the porous element 3 within the vessel, e.g., provide an air-tight seal. While in this embodiment, the cap 2 threadedly engages with the vessel 4, other engagements are possible, such as interference or other frictional fit (e.g., an o-ring or gasket on the cap may engage an inner wall of the vessel 4), bayonet connection, snap fit, etc. The porous element 3 may be suspended in the vessel 4 as shown, and may be positioned in a known and repeatable way within the vessel 4. Reliable positioning of the porous element 3 in the vessel may be useful for certain treatment, such as ensuring the sample is suitably positioned relative to a focal zone of acoustic energy. In some embodiments, the vessel 4 may be used to dry and/or store a sample, e.g., in a way similar to that in FIG. 2. However, in this embodiment, the vessel 4 is arranged to hold the sample and a liquid material, such as a reagent used in recovery of biomolecules in a blood sample held by the porous element, for treatment with focused acoustic energy. As discussed in more detail below, focused acoustic energy can be used to recover DNA, proteins and other biomolecules from a blood or other sample in an effective way.

In some embodiments, the sample holder 1 may include a blotter element 5 that is functionally interposed between the porous element 3 and a pool of blood or other liquid from which a sample is to be taken. The blotter element 5 may be arranged in different ways, and in FIG. 5 the blotter element 5 is attached at a distal end 31 of the porous element 3. The blotter element 5 may be arranged to contact the pool of blood or other liquid and wick blood into the blotter element 5 and to the porous element 3. In this way, the porous element 3 need not contact the pool of blood or other sample source directly, e.g., thereby avoiding contamination of the porous element 3 by contact with skin or other surfaces. The blotter element 5 may also function as a kind of filter so that only blood-borne materials under a certain size reach the porous element 3. For example, the blotter element 5 may retain whole blood cells and other blood-borne materials over a threshold size and allow blood serum and other blood-borne materials under the threshold size to reach the porous element 3 so as to be wicked or otherwise held by the porous element 3. The blotter element 5 may be made of any suitable material, and may have any suitable porosity or other characteristic to impede or prevent flow of materials over a desired size through the blotter element 5. Also, the blotter element 5 may be arranged to wick or otherwise receive a defined volume of fluid.

In some embodiments, the blotter element 5 may be separable from the porous element 3. For example, the blotter element 5 may be separated by centrifugation and/or in other ways that avoid any need to physically touch the blotter element 5. In one embodiment, the porous element 3 and attached blotter element 5 may be placed in a vessel like that in FIG. 4 and centrifuged so that the blotter element 5 is pulled from the porous element 3. The separated blotter element 5 may be retained for later use, e.g., to extract DNA or other materials from whole blood cells or other materials captured in the blotter element 5, while the porous element 3 may be used to extract other, smaller materials. In other embodiments, the blotter element 5 may be physically grasped and pulled from the porous element 3, or otherwise separated from the porous element, e.g., by extending a push rod down a center through hole of the porous element 3 and pushing the blotter element 5 away from the distal end 31 of the porous element 3.

Figure 5:
FIG. 5 shows a side view of an illustrative embodiment of a sample holder including a blotter element.
Figure 5:
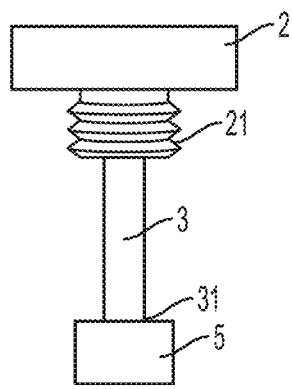
Figure 6:
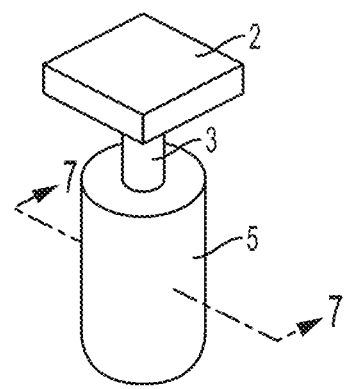
FIG. 6 shows a perspective view of another embodiment including a blotter element.
Figure 7:
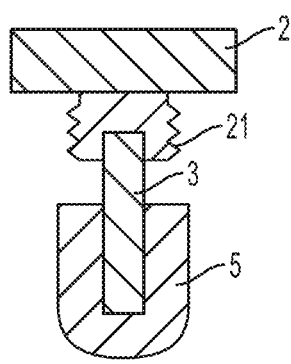
FIG. 7 shows a cross sectional view along the line 7-7 in FIG. 6.

The blotter element 5 may be arranged in other ways than that shown in FIG. 5, such as that shown in FIGS. 6 and 7. In this embodiment, the blotter element 5 forms a type of sheath around the porous element 3, and although not shown, may completely cover the porous element 3. This arrangement may provide a uniform wicking or other travel distance through the blotter element 5 to the porous element 3, which may provide desired flow rates, filtering functions, volume retaining functions, etc., as well as protect the porous element 3 from contact with surfaces other than the blotter element 5. As with the FIG. 5 embodiment, the blotter element 5 may be separated from the porous element 3 by centrifugation, grasping and pulling, etc. The porous element 3 may be stored in a container 7 for drying a blood or other sample either alone, or with a blotter element 5. If stored with the blotter element 5, the blotter element 5 may be separated from the porous element before, during or after drying of the blood sample.

Figure 8:
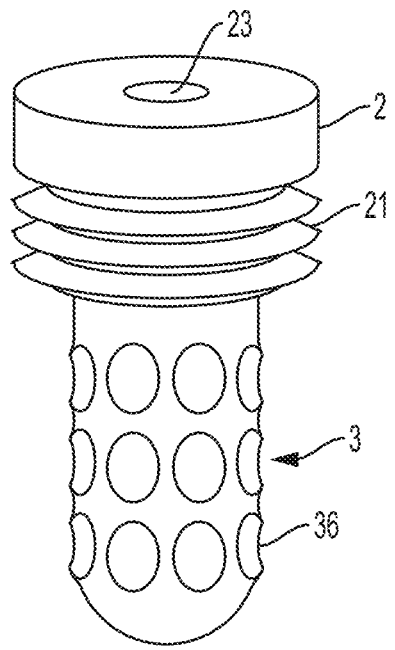
FIG. 8 shows a sample holder having a porous element including a cage.

FIG. 8 shows another illustrative embodiment in which the porous element 3 includes a cage having an inner space in which a blood or other liquid sample is held. The cage may include a plurality of openings 36 that are open to the inner space, which may be empty of any structural material. Thus, for example, the cage may be formed as a hollow tube or well with one or more openings 36 through a wall of the tube or well. The openings 36 and/or other portions of the cage may be arranged to hold a liquid sample, such as wet or liquid blood, by surface tension. That is, surface tension may cause a blood sample to be held in the inner space of the cage such that the blood does not flow through the openings 36. In some embodiments, the cage may have a hydrophobic outer portion and a hydrophilic inner portion that aids in retaining blood in the inner space of the core. In some embodiments, the cage may have a surface texture at an inner side exposed to the inner space that helps to retain blood in the inner space. In other embodiments, a cage may container a fibrous material that retains liquid, such as fibrous material made of polyethylene terephthalate (PET). In another arrangement, a cage may be formed by a braided configuration of polymer or other fibers having a hollow core in which blood may be held. In some embodiments, the hollow core of a braided fiber cage may be at least partially filled with a fibrous material, such as PET fibers mentioned above. In some cases, different types of polymer material fibers have been found to aid in improved recovery of nucleic acid, protein and other material from dried blood and other samples.

A blood or other liquid sample may be dispensed into the inner space of the cage, e.g., via a port 23 of the cap that allows access to the inner space. The port 23 may be part of a septum that is normally closed but allows passage of a pipette tip to dispense blood into the cage so the porous element can hold the blood. Alternately, blood may be provided into the inner space via one or more of the openings 36. With the blood sample held by the cage, the blood sample may be dried, e.g., while stored in a container 7. The openings 36 may provide air or other gas exposure surfaces for the blood, and thus aid in drying of the sample.

As in the sample holders discussed above, a porous element 3 including a cage like that in FIG. 8 holding a dried blood sample may be positioned in a vessel 4. The dried blood sample may be exposed to focused acoustic energy to dislodge the sample from the cage, allowing the dried sample to drop into an extraction buffer or other liquid in the vessel 4 so that the sample can be rehydrated. Alternately, the dried sample may be immersed in the buffer or other liquid while held by the cage.

Figure 9:
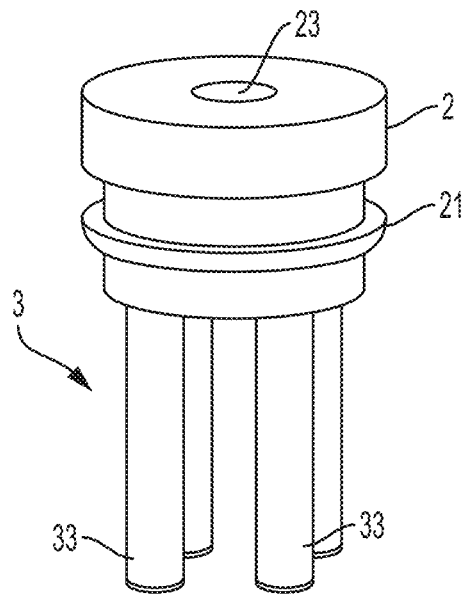
FIG. 9 shows a side view of a sample holder having a porous element arranged with five rods configured to hold a liquid sample in spaces between the rods.
Figure 10:
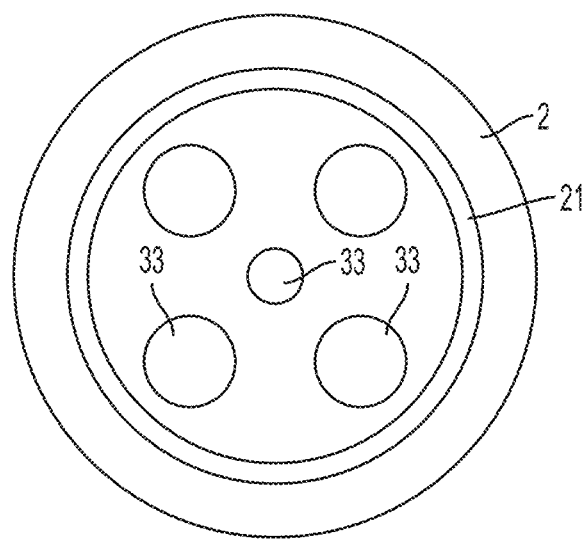
FIG. 10 shows a bottom view of the FIG. 9 embodiment.

FIGS. 9 and 10 show another illustrative embodiment of a porous element 3 that includes a cage. In this embodiment, the cage is formed by five rods 33 that extend downwardly from a cap 2. The rods 33 and spacing between the rods may be arranged to hold a blood sample by surface tension. For example, a blood sample may be dispensed into a port 23 of the cap 2 and held in the inner space of the porous element 3 between the rods 33. In one embodiment, four rods positioned at an outer periphery of the cage may be formed of or include a hydrophobic material, while an inner rod may include a hydrophilic material so that a blood sample or other water-containing sample is held in the space between the rods 33. In one embodiment, the rods 33 may be 1 mm in diameter and 10 mm long, and the rods may be snapped into corresponding recesses in the cap 2. A dried blood sample held by the rods 33 may be dislodged by acoustic energy, physical contact, rehydration or other means.

In some embodiments, a porous element 3 may be made of, or otherwise include, a material that disintegrates or otherwise loses its structural integrity when exposed to focused acoustic energy. That is, the porous element 3 may be physically robust to receive and hold a wet blood sample, and hold the sample during and after drying. When it is wished to recover or otherwise use the dried blood sample, the porous element 3 may be placed in a vessel 4 and exposed to focused acoustic energy. This may cause the porous element 3 to fall apart or otherwise lose its structural integrity so that the blood sample is released. In some cases, the porous element 3 may be made of a fiber glass material arranged to break down in the presence of acoustic energy. With the blood sample released, it may be rehydrated or otherwise processed. Components of the disintegrated porous element 3 may be separate from the blood sample, e.g., by centrifugation.

The inventors have appreciated that it would be advantageous to employ focused acoustic energy in processing biological samples such as dried blood samples to extract and recover biomolecules efficiently and effectively. While a sample holder arranged in accordance with aspects of the invention described in connection with FIGS. 1-10 may provide improved performance in extraction and recovery, extraction and recovery techniques employing focused acoustic energy described herein can be used with samples held by a variety of different arrangements, such as dried blood spots held on a paper substrate (e.g., in which blood is dried in or on the substrate and stored for later processing and analysis). Upon exposure to the focused acoustic energy, portions of the blood (e.g., cells, plasma) may be separated from the substrate and further processed (e.g., cell lysis, DNA shearing/fragmentation, etc.) via the focused acoustic treatment. Or, in some cases, certain portions of the blood may be processed while adhered to the paper or other substrate. The recovered biomolecules from the sample may be of a high enough yield and quality so as to be immediately suitable for high-throughput analysis (e.g., via NGS, PCR, etc.). This is in contrast with conventional extraction methods that do not employ focused acoustics in the manner described herein. Such conventional extraction methods have been observed to result in the recovery of biomolecules having a comparatively lower yield (e.g., recovery by mass) and lower quality (e.g., a lower percentage of DNA which is PCR amplifiable), which is unsuitable for certain types of high-throughput analysis, such as NGS.

Figure 11:
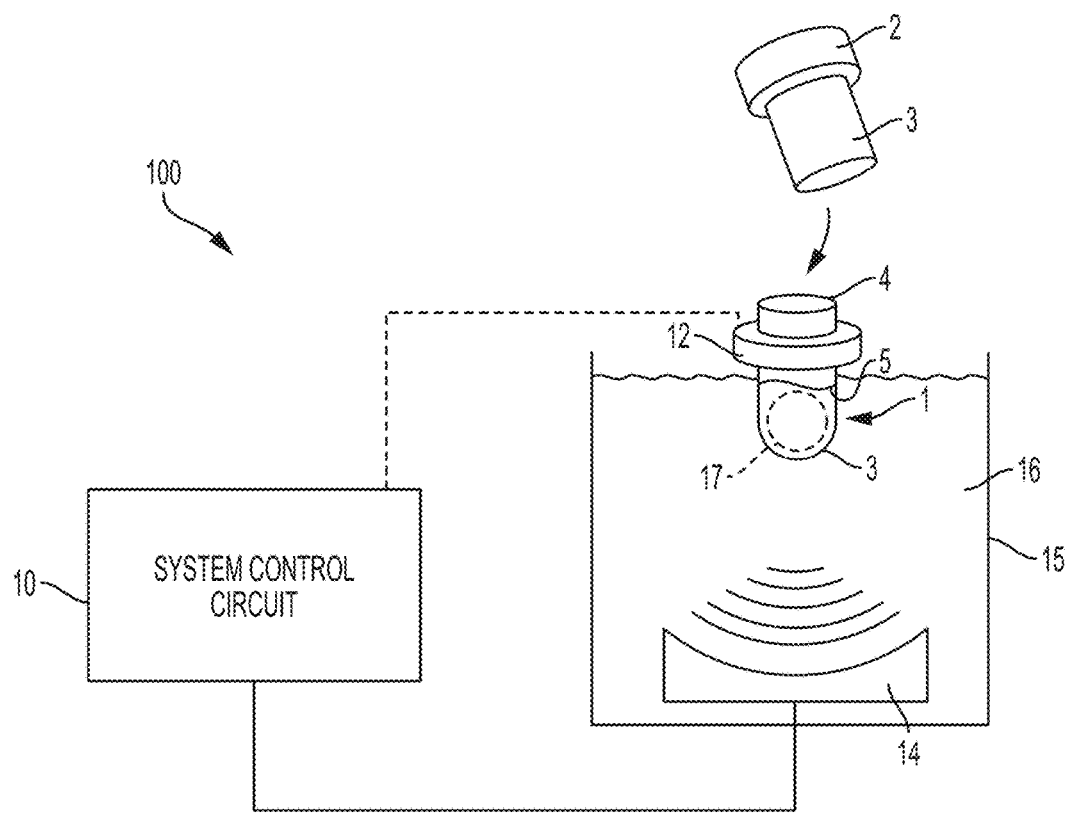
FIG. 11 shows a schematic block diagram of an acoustic treatment system that incorporates one or more aspects of the present disclosure.

FIG. 11 shows a schematic block diagram of an acoustic treatment system 100 that incorporates one or more aspects of the present disclosure and/or can be employed with one or more aspects of the described herein. It should be understood that although embodiments described herein may include most or all aspects of the invention(s), aspects of the invention(s) may be used alone or in any suitable combination with other aspects of the invention(s).

In this illustrative embodiment, the acoustic treatment system 100 includes an acoustic energy source with an acoustic transducer 14 (e.g., including one or more piezoelectric elements) that is capable of generating an acoustic field (e.g., at a focal zone 17) suitable to cause mixing, e.g., caused by cavitation, and/or other affects on a sample contained in a vessel 4. The sample may include solid particles or other material on a porous element 3, and/or liquid material in the vessel. Acoustic energy may be transmitted from the transducer 14 to the vessel 4 through a coupling medium 16, such as a liquid (e.g., water), a gel or other semi-solid, or a solid, such as a silica, metal or other material. Where the coupling medium 16 is a liquid, a coupling medium container 15 may be used to hold the coupling medium 16.

The vessel 4 may have any suitable size or other arrangement, e.g., may be a glass or metal tube, a plastic container, a well in a microtiter plate, a vial, or other, and may be supported at a location by a vessel holder 12. Although a vessel holder 12 is not necessarily required, the vessel holder 12 may interface with the control circuit 10 so that the vessel 4 and the sample in the vessel is positioned in a known location relative to an acoustic field, for example, at least partially within a focal zone of acoustic energy. In this embodiment, the vessel 4 is a 130 microliter borosilicate glass tube, but it should be understood that the vessel 4 may have other suitable shapes, sizes, materials, or other feature, as discussed more below. For example, the vessel 4 may be a cylindrical tube with a flat bottom and a threaded top end to receive a cap 2, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes.

The transducer 14 can be formed of a piezoelectric material, such as a piezoelectric ceramic. In some embodiments, the ceramic may be fabricated as a "dome," which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing or undamped to increase power output. The response may be linear if not overdriven. The high-energy focus zone of one of these domes may be cigar-shaped. At 1 MHz, the focal zone is about 6 cm long and about 2 cm wide for a 20 cm dome, or about 15 mm long and about 3 mm wide for a 10 cm dome. The peak positive pressure obtained from such systems is about 1 MPa (mega Pascal) to about 10 MPa pressure, or about 150 PSI (pounds per square inch) to about 1500 PSI, depending on the driving voltage. The focal zone, defined as having an acoustic intensity within about 6 dB of the peak acoustic intensity, is formed around the geometric focal point. It is also possible to generate a line-shaped focal zone, e.g., that spans the width of a multi-well plate and enables the system 100 to treat multiple samples simultaneously. Other arrangements for producing focused acoustic energy are possible. For example, a flat transducer may be provided with a tapered waveguide for focusing or otherwise channeling acoustic energy emitted from the transducer toward a relatively small space where the sample and vessel are located.

To control an acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. Moreover, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others. Thus, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

Under the control of a control circuit 10, the acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample. The focal zone 17 may be larger than the sample volume, or may be smaller than the sample volume, as shown in FIG. 11. U.S. Pat. Nos. 6,948,843 and 6,719,449 are incorporated by reference herein for details regarding the construction and operation of an acoustic transducer and its control.

In various embodiments, the sample may include blood deposited or otherwise located on the surface and/or pores of a substrate, e.g., a dried blood sample held by a porous element 3 and/or blotter element 5. The sample may further include a solution or mixture that is suitable for lysing blood cells and extracting target biomolecules (e.g., DNA, RNA, protein, etc.). In some embodiments, the liquid in the vessel 4 includes a buffer, such as water along with a detergent, e.g., a 0.25% SDS (sodium dodecyl sulfate), tritonX100, NDSB (non-detergent sulfobetaine), etc. solution, although other solutions are possible, such as ethanol and/or other suitable buffer solutions, an enzyme-containing solution, etc.

In an embodiment where the acoustic treatment system 100 is a Covaris S220 or E220 model, acoustic treatment may be applied using a 10% duty cycle, a peak incident power of 175 watts, 200 cycles per burst, for a suitable period of time (e.g., 120 seconds or more, approximately 360 seconds or more, etc.). Of course, other duty cycles, peak power, cycles per burst and/or time periods may be used to produce a sufficient amount of power for processing the blood sample. For example, to achieve desirable results with regard to extraction and recovery of biomolecules from the blood sample and with regard to quality of the extracted biomolecules, the acoustic transducer may be operated at a peak intensity power of between 100 W and 300 W, a duty factor of between 10% and 90% and a cycles per burst of between 100 and 300, for an appropriate duration of time. It can be appreciated that the acoustic transducer may be operated so as to produce focused acoustic energy that results in a suitable level of energy input to the sample material. After acoustic energy treatment is complete, the porous element 3 may be centrifuged to pull materials from the porous element 3 for collection by a vessel 4 in which the porous element 3 is located.

In some embodiments, the transducer may generate acoustic energy having a peak incident power over the course of a period of time that produces a particular amount of energy, to achieve preferred results. As described herein, the peak incident power (PIP) is the power emitted from the transducer during the active period of one cycle. The peak incident power, in some cases, may control the amplitude of the acoustic oscillations. The energy applied to the sample material may be determined from the peak incident power of the applied acoustic energy and the duration of the acoustic treatment period. In some embodiments, to suitably lyse cells and extract or otherwise operate on the target biomolecule(s) from a dried blood sample, the acoustic transducer may be operated so as to generate focused acoustic energy according to a peak incident power of greater than or equal to 50 Watts, greater than or equal to 100 Watts, greater than or equal to 150 Watts, greater than or equal to 200 Watts, greater than or equal to 250 Watts, greater than or equal to 300 Watts, or other values outside of these ranges.

The acoustic transducer may be operated at a suitable duty factor, in combination with other parameters, to generate focused acoustic energy that leads to preferred results. As described herein, the duty factor is the percentage of time in a cycle in which the transducer is actively emitting acoustic energy. For example, a duty factor of 60% refers to the transducer being operated in an "on" state 60% of the time, and in an "off" state 40% of the time. In some embodiments, in appropriately lysing cells and extracting/processing the target biomolecule(s) from the dried blood sample, the acoustic transducer may be operated at a duty factor setting of greater than or equal to 10%, greater than or equal to 20%, greater than or equal to 30%, greater than or equal to 40%, greater than or equal to 50%, greater than or equal to 60%, greater than or equal to 70%, or greater than or equal to 80%, or other values outside of these ranges.

The acoustic transducer may be operated according to a suitable cycles-per-burst setting to achieve preferred results. As described herein, the cycles per burst (CPB) is the number of acoustic oscillations contained in the active period of one cycle. In some embodiments, to lyse and extract/process the target biomolecule(s) from the dried blood sample, the acoustic transducer may be operated to generate focused acoustic energy according to a cycles per burst setting of greater than or equal to 50, greater than or equal to 100, greater than or equal to 150, greater than or equal to 200, or other values outside of these ranges.

After a suitable degree of focused acoustic treatment, as noted above, various enzymes or other agents may be activated and/or accelerated, resulting in the removal of certain molecules or contaminants from the mixture. For instance, as noted above, when seeking to recover nucleic acids from the sample, it may be preferable to include Proteinase K within the mixture, and accelerating enzymatic activity thereof by adjusting the temperature of the sample to approximately 56 degrees C.

When seeking to recover DNA from the sample, any suitable DNA purification protocol may be used. As an example of a DNA purification step, the sample may be centrifuged and transferred to a tube (e.g., 1 mL microfuge tube) to which a suitable binder (e.g., binding binder) and solvent (e.g., ethanol) is added and mixed. The sample may then be centrifuged and subsequently transferred to a purification column where the DNA binds thereto. The assembly may further be centrifuged and washed using appropriate buffer solutions. The DNA may then be eluted using a suitable elution buffer (e.g., Tris-EDTA, water) for releasing the DNA from the purification column. The DNA/RNA can also be purified using magnetic beads using a known process.

Figure 12:
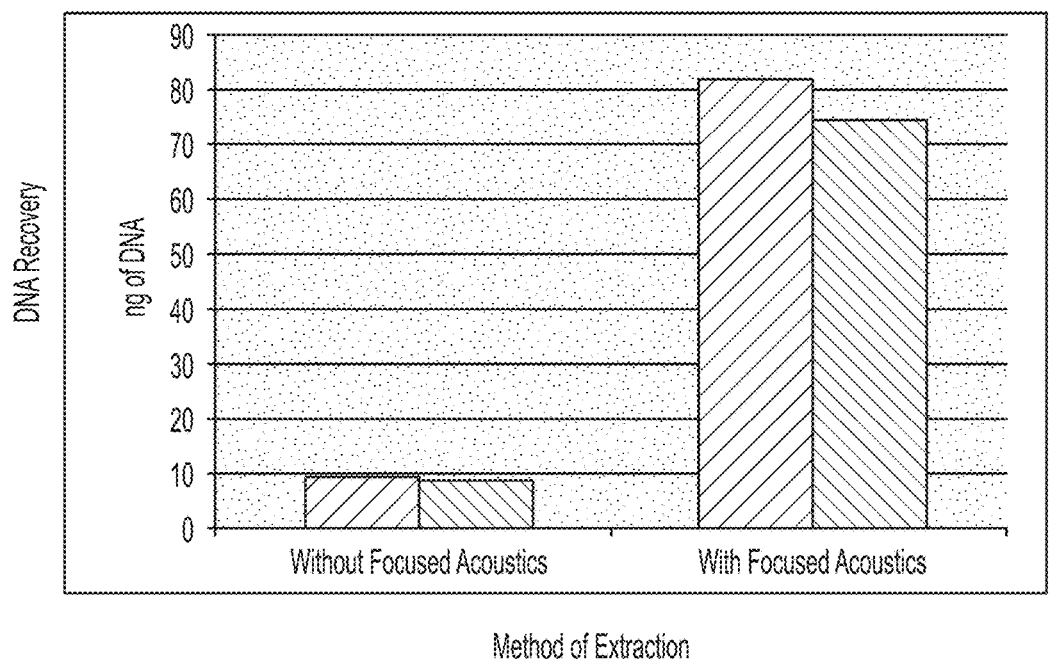
FIG. 12 depicts a comparison between amounts of DNA recovered with and without focused acoustics in accordance with some embodiments.

FIG. 12 shows a graph that depicts results from an example that compares the amount of DNA recovered from dried blood samples for a passive extraction protocol, which does not use focused acoustics, and an active extraction protocol, which employs focused acoustics. In this example, both protocols involved extraction and recovery of DNA from a dried blood spot corresponding to approximately 5 microliters of fresh blood that has been dried on to a 3 mm diameter punch Guthrie card. The respective dried blood spots were placed in a Covaris microTUBE vessel along with an extraction mixture including appropriate amounts of SDS buffer solution, lysis buffer and Proteinase K.

In the passive extraction protocol (corresponding to bar graphs in FIG. 12 labeled "Without Focused Acoustics"), focused acoustics was not employed, and the blood spot sample was allowed to sit within the extraction mixture in the vessel for 1 hour at room temperature. In the active extraction protocol (corresponding to bar graphs in FIG. 12 labeled "With Focused Acoustics") where focused acoustics was employed, rather than sitting for 1 hour at ambient conditions, the sample was exposed to focused acoustic treatment applied using a 10% duty cycle, a peak incident power of 175 watts, 200 cycles per burst, for approximately 120 seconds. Both extraction protocols were then subject to the same DNA purification steps using a purification column, as described above. As shown, two tests were run for each protocol.

As shown in FIG. 12, the amount of DNA recovered from the dried blood spot corresponding to approximately 5 microliters of fresh blood for the passive extraction protocol (that does not employ focused acoustic energy) performed on two sample runs was about 10 ng or less. In contrast, the amount of DNA recovered from a similar dried blood spot except using the active extraction protocol (employing focused acoustic energy) for two sample runs was approximately 74 ng and 82 ng, respectively. That is, dried blood spot samples extracted via focused acoustics using the active extraction protocol resulted in a yield in DNA recovery of approximately 8 times more than that observed for dried blood spot samples that were not exposed to focused acoustics in the passive extraction protocol.

Figure 13:
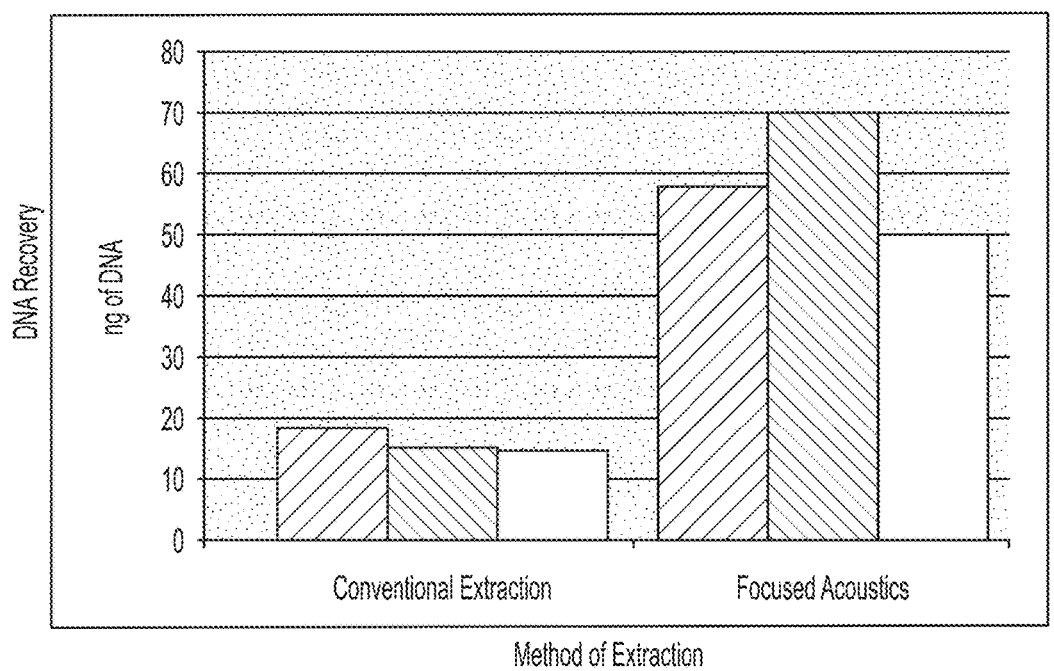
FIG. 13 shows a comparison between amounts of DNA recovered using a conventional extraction method and a focused acoustic extraction method in accordance with some embodiments.

FIG. 13 illustrates a graph that depicts results from an example that compares the amount of DNA recovered for the active extraction protocol using focused acoustic treatment as described above, as compared to a conventional method of DNA extraction (QIAamp DNA Mini Kit provided by Qiagen). As shown, three tests were run for each protocol, and dried blood samples were in the form described in relation to FIG. 12.

As shown in FIG. 13, the amount of DNA recovered from a dried blood spot corresponding to approximately 5 microliters of fresh blood using the conventional DNA extraction kit for three trial runs was about 18 ng, 15 ng and 14 ng, respectively. In contrast, the amount of DNA recovered from a similar dried blood spot for the active extraction protocol employing the focused acoustic energy for three trial runs was approximately 50 ng, 58 ng and 70 ng, respectively. Here, the dried blood spot samples extracted via focused acoustics in the active extraction protocol resulted in a yield in DNA recovery substantially greater (e.g., approximately 3-4 times more) than that observed for dried blood spot samples that were extracted via the conventional DNA extraction method.

It can be appreciated that the active extraction protocol employing focused acoustic treatment provides enhanced ability to recover DNA from dried blood spots. Though, it can be appreciated that depending on the particular sample of blood, the amount of recoverable DNA may vary. In some embodiments, the amount of DNA recovered from a dried blood spot corresponding to 5 microliters of fresh blood by using focused acoustic treatment in accordance with methods described herein may be greater than 20.0 ng (e.g., between 20.0 ng and 160.0 ng, between 20.0 ng and 140.0 ng, between 20.0 ng and 120.0 ng, between 20.0 ng and 100.0 ng, between 20.0 ng and 80.0 ng), greater than 30.0 ng, greater than 40.0 ng, greater than 50.0 ng, greater than 60.0 ng, greater than 70.0 ng, greater than 80.0 ng, greater than 90.0 ng, greater than 100.0 ng, greater than 110.0 ng, greater than 120.0 ng, greater than 130.0 ng, greater than 140.0 ng, greater than 150.0 ng, greater than 160.0 ng, or any other suitable value outside of the above noted ranges.

Figure 14:
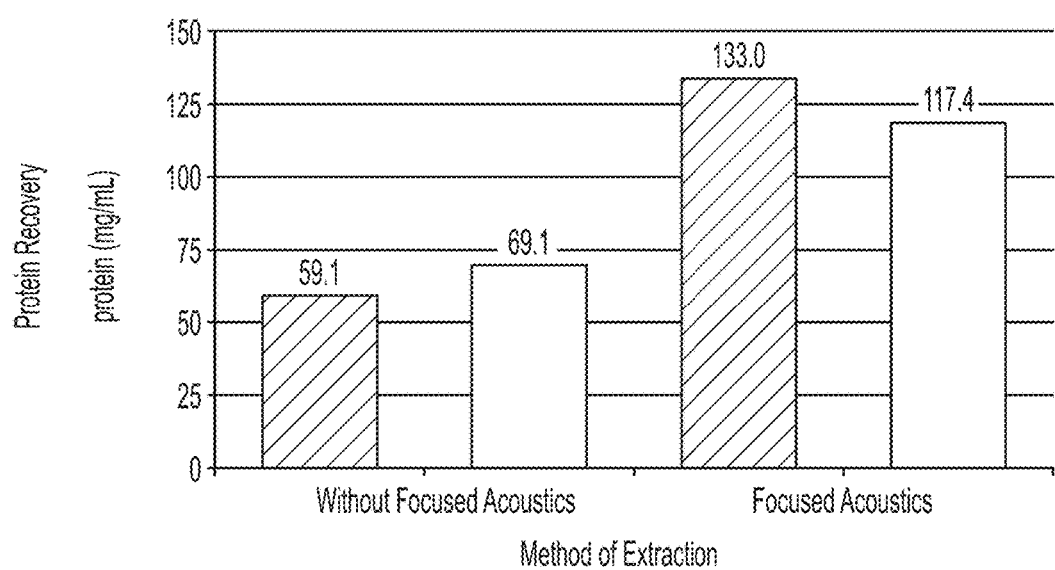
FIG. 14 shows a comparison between amounts of protein recovered with and without focused acoustics in accordance with some embodiments.

Focused acoustical methods in accordance with the present disclosure may also be effective in extraction and recovery of other types of biomolecules, such as proteins. FIG. 14 shows a graph that depicts results from an example that compares the amount of protein recovered for a passive extraction protocol, which does not use focused acoustics, and an active extraction protocol, which uses focused acoustics. In this example, both protocols involved extraction and recovery of protein from a blood spot corresponding to approximately 5 microliters of fresh blood that has been dried on to a 3 mm diameter punch Guthrie card. The dried blood spot was placed in a Covaris microTUBE vessel along with an extraction mixture including appropriate amounts of SDS buffer solution and lysis buffer, yet without Proteinase K.

Except for the absence of Proteinase K, the passive and active extraction protocols employed were similar to that described above with respect to the example of FIG. 12. Hence, in the passive extraction protocol (corresponding to bar graphs in FIG. 14 labeled "Without Focused Acoustics") where focused acoustics was not employed, the dried blood spot sample was placed within the extraction mixture for 1 hour at room temperature. In the active extraction protocol (corresponding to bar graphs in FIG. 14 labeled "With Focused Acoustics") where focused acoustics was employed, the sample was exposed to focused acoustic treatment similar to that discussed above for DNA extraction. Rather than using a purification column, which was employed for nucleic acid recovery, both protocols represented in FIG. 14 involved a Bradford assay which includes a spectroscopic analysis that measures the concentration of protein within the solution. As shown, two tests were run for each protocol.

FIG. 14 depicts the respective protein concentration of the samples recovered from a dried blood spot corresponding to approximately 5 microliters of fresh blood for both the passive and active extraction protocols. For the passive extraction protocol, the protein concentration of the final solution was measured for two trial runs to be 69.1 mg/mL and 59.1 mg/mL which, for a vessel volume of 110 microliters, corresponds to protein yields of 7.6 mg and 6.5 mg, respectively. By contrast, for the active extraction protocol, where focused acoustic treatment is applied, the protein concentration of the final solution for two trial runs was measured to be 133.0 mg/mL and 117.4 mg/mL. For a vessel volume of 110 microliters, these values correspond to respective protein yields of approximately 14.6 mg and 12.9 mg. Accordingly, dried blood spot samples extracted using focused acoustics in the active extraction protocol resulted in a yield in protein recovery of more than 2 times greater than that observed for dried blood spot samples that were not exposed to focused acoustics in the passive extraction protocol.

Similarly to that with respect to DNA extraction, use of the active extraction protocol employing focused acoustic treatment results in an enhanced ability to recover protein from dried blood spots. It can be appreciated that the amount of recoverable protein may vary depending on the particular sample of blood. In some embodiments, the amount of protein recovered by using focused acoustic treatment in accordance with methods described herein per 5 microliters of fresh blood corresponding to a dried blood spot may be greater than 8.0 mg (e.g., between 8.0 mg and 20.0 mg, between 8.0 mg and 15.0 mg), greater than 9.0 mg, greater than 10.0 mg, greater than 11.0 mg, greater than 12.0 mg (e.g., between 12.0 mg and 20.0 mg, between 12.0 mg and 15.0 mg), greater than 13.0 mg, greater than 14.0 mg, greater than 15.0 mg, or any other suitable value outside of the above noted ranges.

Figure 15:
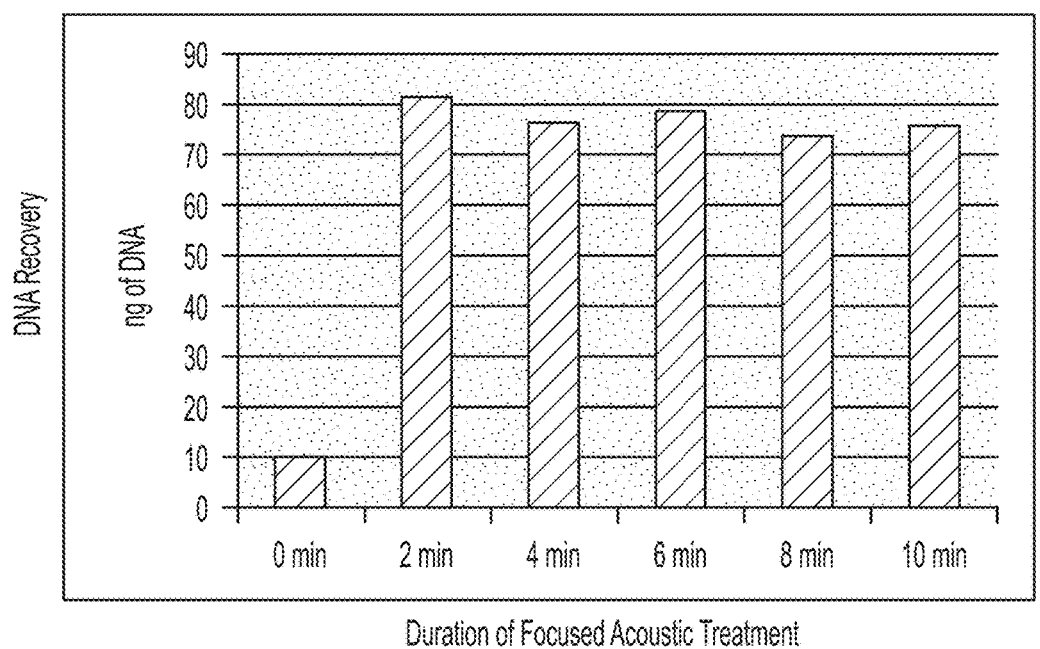
FIG. 15 depicts amounts of DNA recovered using focused acoustic extraction methods at various time intervals in accordance with some embodiments.

Exposure to a suitable level of focused acoustic energy may be helpful in bypassing a number of steps of protocol (e.g., high temperature incubation, chemical treatments, etc.) that may otherwise be required for extraction (or other processing) without the focused acoustic energy. As noted below, the focused acoustic energy may be further beneficial not only in extracting target biomolecules but also in processing the biomolecules, such as shearing and fragmentation of nucleic acids. The processing time for the target biomolecule(s) to be extracted from the sample of blood may be relatively short. For instance, as discussed above, the time under which the sample may be exposed to the focused acoustic energy for suitable recovery of the biomolecule(s) may be as low as 2 minutes. FIG. 15 depicts a graph that shows the amount of DNA recovered from a dried blood spot corresponding to 5 microliters of fresh blood using methods described above, depending on the duration of focused acoustic processing.

As shown, when the blood sample was not exposed to focused acoustic energy (i.e., duration of focused acoustic treatment is 0 minutes), only approximately 10 ng of DNA was recovered. This protocol is similar to the passive extraction protocol of FIG. 12 (labeled "Without Focused Acoustics"). However, when the blood sample was exposed to just 2 minutes of focused acoustic energy, over 80 ng of DNA was recovered, similar to the active extraction protocol of FIG. 12 (labeled "With Focused Acoustics"). Moreover, the amount of DNA recovered upon exposure to focused acoustic energy for increasing periods of time resulted in approximately the same amount of recovered DNA. For instance, when the blood sample was exposed to 4 minutes, 6 minutes, 8 minutes and 10 minutes of focused acoustic energy, respectively, the amount of recovered DNA was within about 10% of the amount of DNA recovered when the sample was exposed to 2 minutes of focused acoustics. This shows that only a short duration of focused acoustic energy may be required for the maximum amount of DNA to be recovered from a given blood sample.

Figure 16:
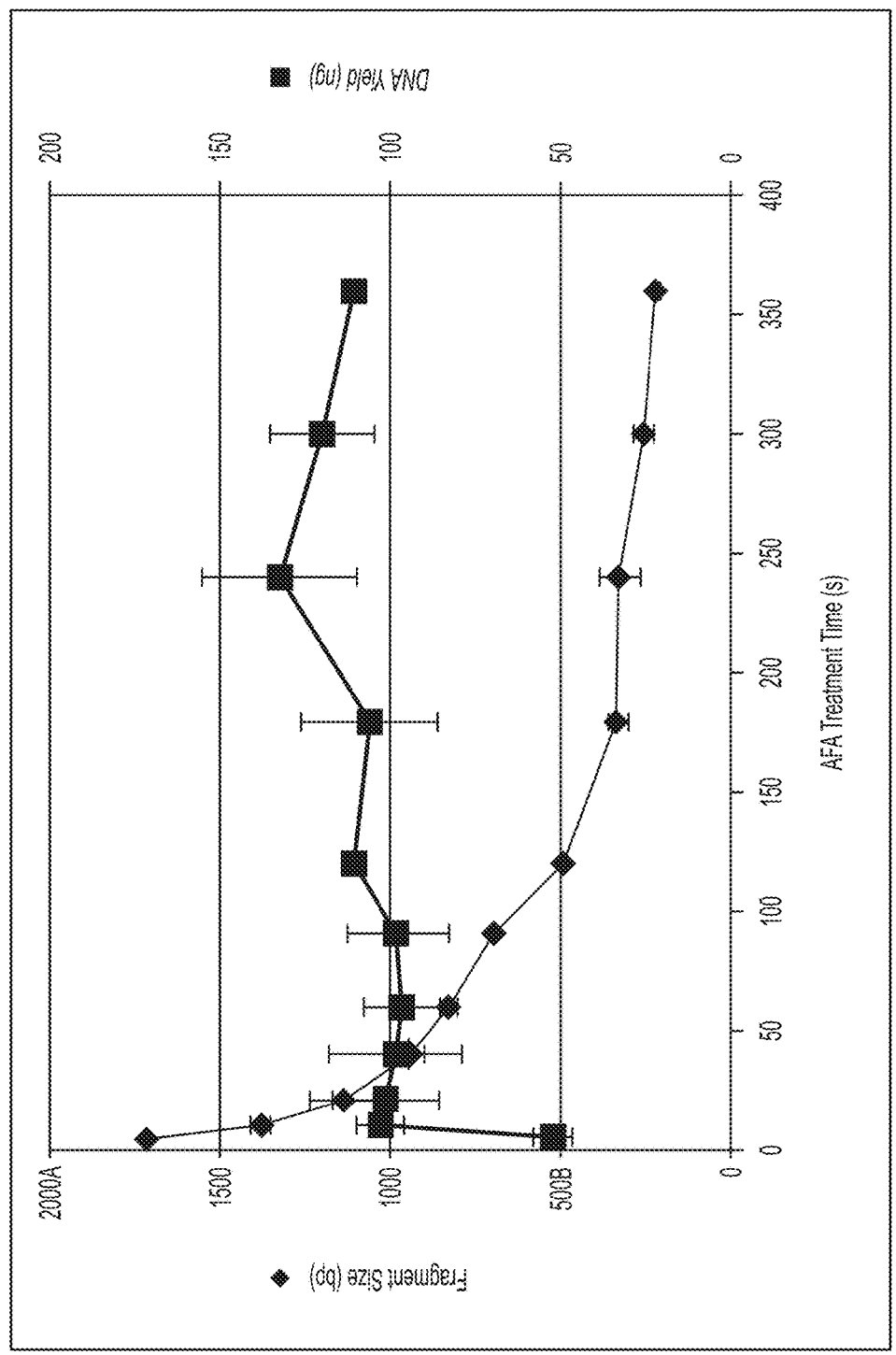
FIG. 16 shows an example depicting a relationship between DNA fragment size and DNA yield for different acoustic energy processing times.

It should also be appreciated that for various embodiments, the duration of time in which the sample is subject to focused acoustic treatment may affect the average DNA fragment size. That is, the focused acoustic processing not only provides for extraction of the target biomolecules (i.e., nucleic acids), but also for shearing and fragmenting thereof. For example, the average DNA fragment size may decrease as the duration of acoustic energy treatment is increased and, conversely, the resulting average DNA fragment size may be larger for shorter durations of acoustic energy treatment. The average DNA fragment size may be tuned according to the duration of time under which the sample is exposed to a suitable amount of focused acoustic energy. FIG. 16 shows one example treatment illustrating the relationship of DNA yield and fragment size to acoustic treatment time. Processing conditions for this example were the same as that for FIG. 12 in which focused acoustic energy is applied to the sample. As can be seen, the DNA fragment size drops with increased treatment time, but overall DNA yield remains relatively constant with time beyond 10-25 seconds. Hence, aspects of the present disclosure allow for both extraction of DNA as well as shearing/fragmentation of the extracted DNA in a single step of focused acoustic processing. This is in contrast with conventional methods where extraction of DNA and shearing/fragmentation typically occur as separate steps. Moreover, the acoustic energy treatment time can be employed to achieve a desired DNA fragment size.

As noted above, the type of substrate on and/or within which the blood is held may contribute to the overall ability to recover the target biomolecule(s). In some embodiments, a greater level of biomolecule recovery may be achieved for certain substrates than would otherwise be the case for other substrates. For instance, in some embodiments, a greater level of biomolecule recovery may be achieved from a substrate that is highly porous or that has a relatively large average pore size. Or, a greater level of biomolecule recovery may be achieved from a substrate or coating on the substrate made up of a hydrophilic material.

Figure 17:
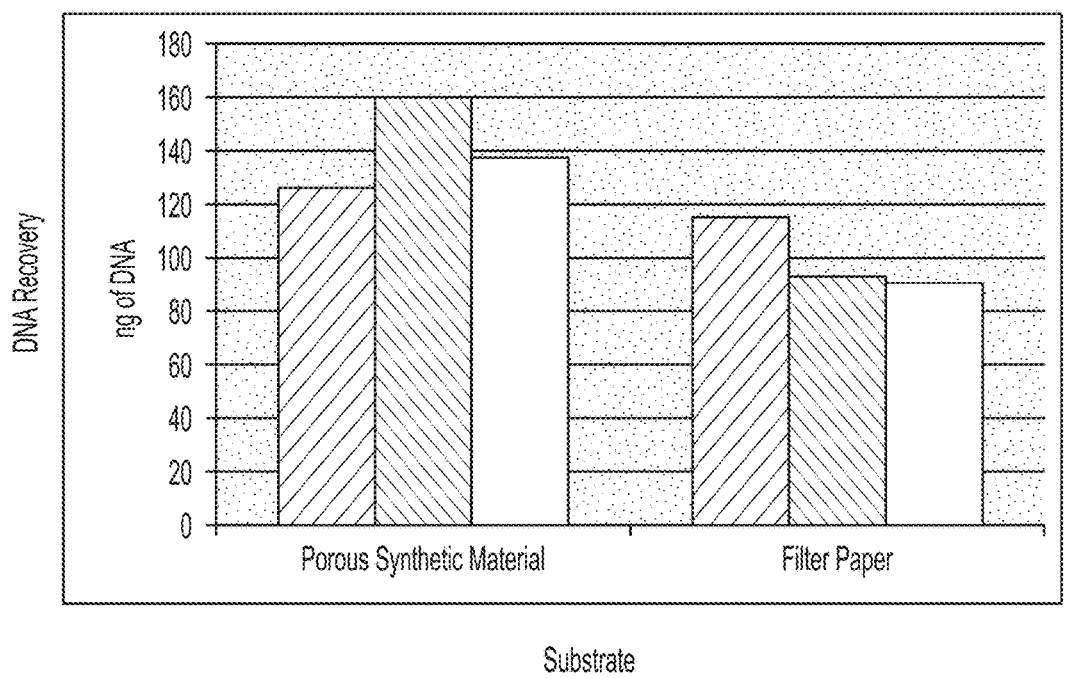
FIG. 17 shows amounts of DNA recovered using focused acoustic extraction methods using various substrates in accordance with some embodiments.

FIG. 17 shows a graph showing data from an example that compares the amount of DNA recovered from 5 microliters of fresh blood spotted on to two different substrates, a porous synthetic material and a filter paper. The samples were immersed in the extraction mixture described above and, in addition, subjected to focused acoustics at a 10% duty cycle, a peak incident power of 175 watts, 200 cycles per burst, for approximately 120 seconds. In this example, the porous synthetic material is a Porex PET fibrous rod, and the filter paper is a Guthrie card. As shown, three trial tests were run for each protocol.

Here, blood samples collected with the porous synthetic material resulted in a greater level of DNA recovery in comparison to blood samples collected with the filter paper. As shown, the amount of DNA recovered from the dried blood spot corresponding to approximately 5 microliters of fresh blood blotted on to the filter paper for three trial tests was approximately 90 ng, 95 ng and 118 ng, whereas the amount of DNA recovered from the dried blood spot corresponding to approximately 5 microliters of fresh blood blotted on to the porous synthetic material for three trial tests was substantially greater, approximately 125 ng, 140 ng and 160 ng. Thus, the type of substrate that holds the blood spotted thereon may influence the overall recovery of biomolecules from the blood sample. In some embodiments of a sample holder, such as that in FIGS. 1-10, the choice of material for the porous element 3 may influence biomolecule recovery, at least when applied to blood samples.

In accordance with aspects of the present disclosure, due to exposure to a suitable level of focused acoustic treatment, the overall quality (e.g., ability to be amplified via PCR) of the biomolecule(s) extracted from the blood sample may be higher than the quality that would arise with a different treatment. That is, a greater percentage of nucleic acid extracted via the focused acoustic energy may be capable of amplification via polymerase chain reaction than nucleic acid extracted without the focused acoustic energy. For example, as noted above, the majority of the nucleic acid (e.g., DNA, RNA) extracted and recovered using a suitable protocol involving focused acoustics may be capable of amplification via PCR. In some embodiments, greater than 50%, greater than 60%, greater than 70%, greater than 80%, greater than 90%, greater than 95%, up to 99% or 100% of the recovered nucleic acid is capable of such amplification.

Figure 18:
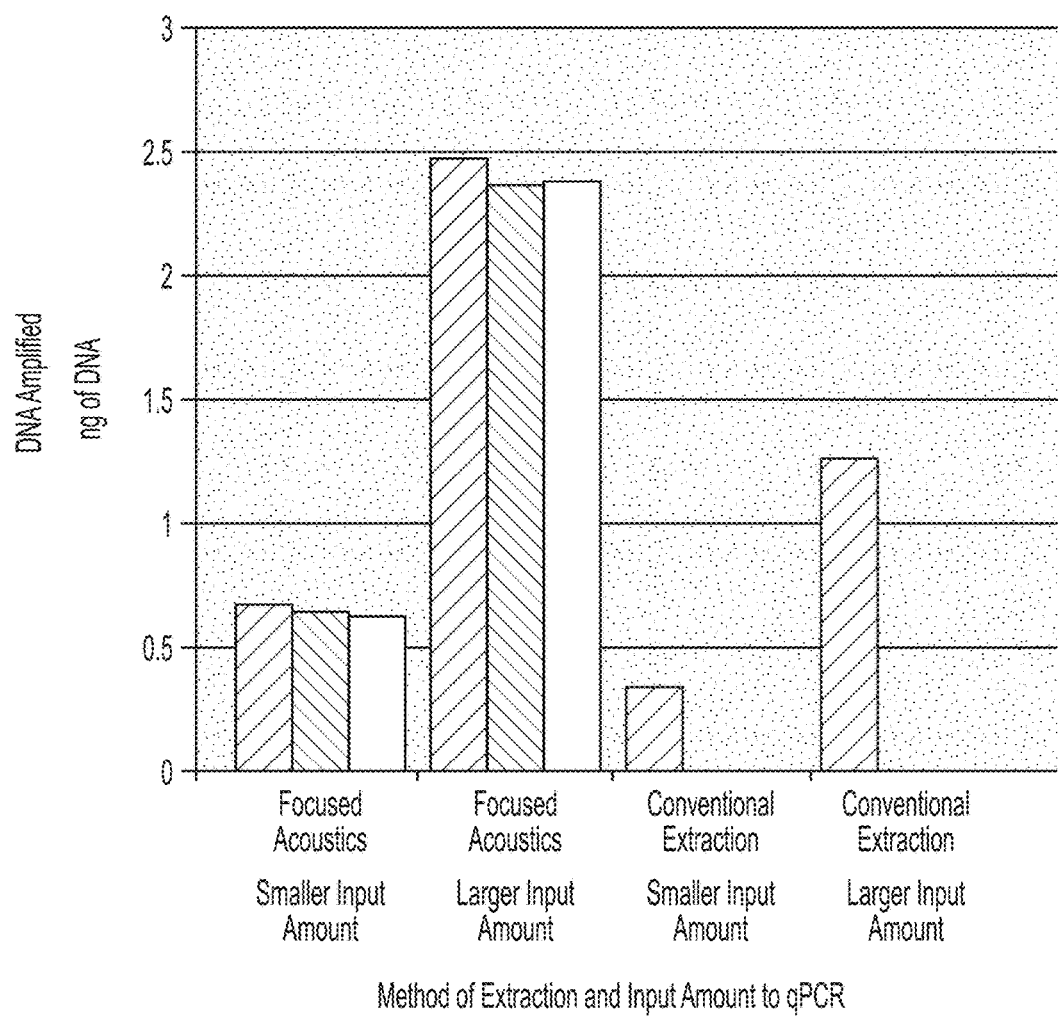
FIG. 18 depicts amounts of DNA amplified using quantitative polymerase chain reaction from various inputs of recovered DNA in accordance with some embodiments.

FIG. 18 shows a graph that shows results from an example of the amount of amplifiable or otherwise useable DNA recovered from different extraction methods as estimated from amplification of a 67-base pair amplicon via qPCR. In particular, a comparison was made of the amount of DNA that is amplifiable or otherwise useable, as recovered from an active extraction protocol that employs focused acoustics and a conventional extraction protocol (QIAamp DNA Mini Kit provided by Qiagen) that does not employ any such focused acoustic energy.

As provided herein, the QIAamp DNA Mini Kit involves the following steps. A dried blood spot sample is placed within a 1.5 mL microcentrifuge tube with 180 microliters of tissue lysis buffer (Qiagen Buffer ATL) and incubated at 85 degrees C. for 10 minutes. The tube is briefly centrifuged to remove drops from inside the lid. 20 microliters of proteinase K stock solution is added to the solution, which is mixed by vortexing, further incubated at 56 degrees C. for 1 hour, and followed by a brief centrifuge step. 200 microliters of a lysis buffer (Qiagen Buffer AL) is added to the mixture, which is mixed by vortexing, incubated at 70 degrees C. for 10 minutes, and followed by a brief centrifuge. 200 microliters of ethanol is then added to the solution, which is mixed by vortexing, and followed by a brief centrifuge step. This mixture is applied to a spin column (QIAamp Mini spin column in a 2 mL collection tube) and centrifuged at 8,000 rpm (6,000 g) for 1 minute. The spin column is removed from the filtrate and placed in a clean 2 mL collection tube. 500 microliters of wash buffer (Qiagen Buffer AW1) is added to the mixture and centrifuged at 8,000 rpm (6,000 g) for 1 minute. The spin column is removed from the filtrate and placed in another clean 2 mL collection tube. 500 microliters of wash buffer (Qiagen Buffer AW2) is subsequently added to the mixture and centrifuged at 14,000 rpm (20,000 g) for 3 minutes. The spin column is removed from the filtrate, placed in another 2 mL clean collection tube and centrifuged at full speed for 1 minute. The spin column is removed from the filtrate and then placed in a clean 1.5 mL microcentrifuge tube. 150 microliters of elution buffer (Qiagen Buffer AE) or distilled water is added to the mixture. The mixture is incubated at room temperature (15-25 degrees C.) for 1 minute and then centrifuged at 8,000 rpm (6,000 g) for 1 minute. The DNA is then collected for further processing.

In the example of FIG. 18, for DNA recovered from each of the above protocols, the amount of DNA was estimated via fluorometric quantitation with a double-stranded-DNA specific dye, and various amounts of DNA were input into a qPCR reaction (SYBR Green qPCR). In particular, a smaller amount (estimated to be approximately 0.5 ng) and a larger amount (estimated to be approximately 2.0 ng) of DNA were input, as recovered from the active extraction protocol and the conventional extraction protocol.

In addition, DNA recovered from the conventional extraction protocol was further sheared to an average fragment size of 200 bp, comparable to the average DNA fragment size provided from the active extraction protocol. In the qPCR analysis, those of skill in the art will appreciate that the number of PCR cycles needed for amplification of the DNA to reach the logarithmic phase (the Ct value) is linearly related to the logarithm of the amount of amplifiable DNA that was added to the reaction. By comparing the Ct values obtained for DNA as recovered from the active extraction protocol and the conventional extraction protocol to Ct values obtained for high-quality genomic DNA sheared to an average fragment size of 200 bp, the amount of high-quality DNA present in the DNA recovered from the active extraction protocol and the conventional extraction protocol could be estimated. By comparing the amount of input DNA estimated from qPCR analysis to the amount of input DNA estimated from fluorometric quantitation, the proportion of total DNA that is amplifiable can be estimated.

Whether or not a sample of DNA is capable of amplification depends, at least in part, on the overall quality of the DNA. For example, damage or contamination will lower the quality of a sample of DNA such that the sample is less likely to be amplified via PCR. DNA that is undamaged and/or more pure is more likely to be amplified via PCR. For example, DNA amplification can be slowed or prevented by the presence of substance(s) that can inhibit or interfere with the polymerase enzyme used in PCR, where such substances can be a by-product of the process of extracting DNA from blood dried onto a substrate.

As shown in FIG. 18, for the smaller input amount of DNA recovered via the active extraction protocol, the amount of amplifiable DNA for three trial runs was determined via qPCR to be approximately 0.6 ng. For the same input amount of DNA recovered via the conventional extraction protocol, the amount of amplifiable DNA was determined via qPCR to be approximately 0.3 ng. Thus, the amount of DNA recovered using focused acoustical methods that is capable of amplification via qPCR is approximately double that of the amount of DNA recovered using conventional extraction methods. Further, as fluorometric quantitation estimates the amount of DNA input into qPCR to be approximately 0.5 ng, the 0.6 ng output from qPCR of DNA extracted via focused acoustics implies that all or nearly all of the DNA recovered from the active extraction protocol is amplifiable or otherwise useable.

Similarly, as further shown in FIG. 18, for the larger input amount of DNA recovered via the active extraction protocol, the amount of amplifiable DNA was determined via qPCR to be as high as approximately 2.4 ng. For the same input amount of DNA recovered via the conventional extraction protocol, the amount of amplifiable DNA was determined via qPCR to be approximately 1.2 ng. Hence, approximately double the amount of DNA recovered via the active extraction protocol employing focused acoustics is capable of amplification in comparison to the amount of DNA recovered via the conventional extraction protocol that is capable of amplification. In addition, similar to that discussed above, fluorometric quantitation estimates the amount of DNA input into qPCR to be approximately 2.0 ng, and so the 2.4 ng output from qPCR of DNA extracted via focused acoustics implies that all or nearly all of the DNA recovered from the active extraction protocol is amplifiable or otherwise useable.

Accordingly, as determined via qPCR, the amount of DNA that is capable of amplification as recovered from focused acoustical methods is significantly greater than the amount of DNA that is capable of amplification as recovered from conventional extraction. Such a finding suggests that the quality and/or purity of DNA recovered from the conventional extraction protocol could be low in comparison to that of DNA which is recovered via focused acoustics and/or that substances that inhibit and/or interfere with the polymerase enzyme used in the qPCR reaction could be present in the DNA recovered by the conventional extraction protocol.

As noted above, focused acoustic methods in accordance with the present disclosure may be more effective and efficient in extracting nucleic acid (e.g., DNA) from a sample of dried blood than conventional extraction protocols, such as from a QIAamp DNA Mini Kit, which does not use such focused acoustic energy. In some embodiments, more nucleic acid extracted from a dried blood sample via methods of focused acoustic energy described herein is capable of amplification via polymerase chain reaction than nucleic acid extracted from an identical dried blood sample using extraction protocol from a QIAamp DNA Mini Kit by greater than 20%, greater than 30%, greater than 40%, greater than 50%, greater than 60%, greater than 70%, greater than 80%, greater than 90%, greater than 100%, greater than 120%, greater than 140%, greater than 160%, greater than 180%, greater than 200%; and/or less than 250%, less than 200%, less than 150%, less than 100%, less than 50%, or less than 20%. Certain combinations of the above-noted percentage ranges may be possible (e.g., between 20% and 100%, between 50% and 150%, etc.).

As determined herein, extraction of biomolecules from dried blood spots via an appropriate level of focused acoustics provides for greater yield and higher quality that would otherwise be the case without such processing. This may open the door for blood spots to be a sufficient source input for higher throughput analytical methods. Such methods may include NGS where a sufficient amount of high quality DNA may be required to determine the presence of specific gene sequences, for example, in early detection disease screening for newborn babies. DNA extracted from dried blood spots (which can easily be captured at birth) is generally stable and independent of the source's age and condition. However, unlike traditional methods of DNA isolation and purification, aspects of the present disclosure allow for efficient and effective processing of blood spots to a degree where NGS and other such methods may now be possible for relatively low volume samples. The quality of DNA extracted using conventional methods is often unsuitable and can give rise to sequencing errors.

Experiments were also conducted to compare the extraction and recovery performance of a sample holder arranged like that in FIG. 1 used to collect, dry and store a blood sample with fresh blood. Three relative performance experiments were conducted, i.e., DNA yield, protein yield, and Fragile-X Mental Retardation Protein (FMRP) yield. Fresh blood was collected from a subject using EDTA Vacutainers (Becton-Dickinson, Franklin Lakes, N.J., USA), and all fresh EDTA blood was processed on the day of collection. Dried blood samples were collected using a sample holder arranged like that in FIG. 2 or 3, and dried blood samples were processed one week after collection. Dried blood samples were taken by wicking about 17 microliters of blood into the porous element of a respective sample holder. The QIAamp DNA Micro Kit (Qiagen, Valencia, Calif.) was used for DNA extraction from fresh blood. For dried blood, dried blood sample was placed in a Covaris microTUBE vessel along with an extraction mixture including appropriate amounts of SDS buffer solution, lysis buffer and Proteinase K. For protein extraction, 17 ul EDTA fresh blood or an equivalent amount of dried blood (i.e., a dried blood sample created by receiving 17 microliters of blood into a porous element) were respectively mixed with 100 uL M-PER™ Mammalian Protein Extraction Reagent (ThermoFisher Scientific) in a Covaris microTUBE-130 and processed on a Covaris E220 Focused Ultrasonicator using 75 W PIP, 10% DC, 200 CPB at 20 C. Total protein yield was determined using the QuickStart Bradford Reagent (BioRad, Hercules, Calif.). Concentrations of Fragile-X Mental Retardation Protein (FMRP) were determined using the FMRP ELISA Kit from LifeSpan Biosciences (Seattle, Wash.). The assay was linear over the 1-20 ng/mL range ($r^2$=0.978).

Figure 19:
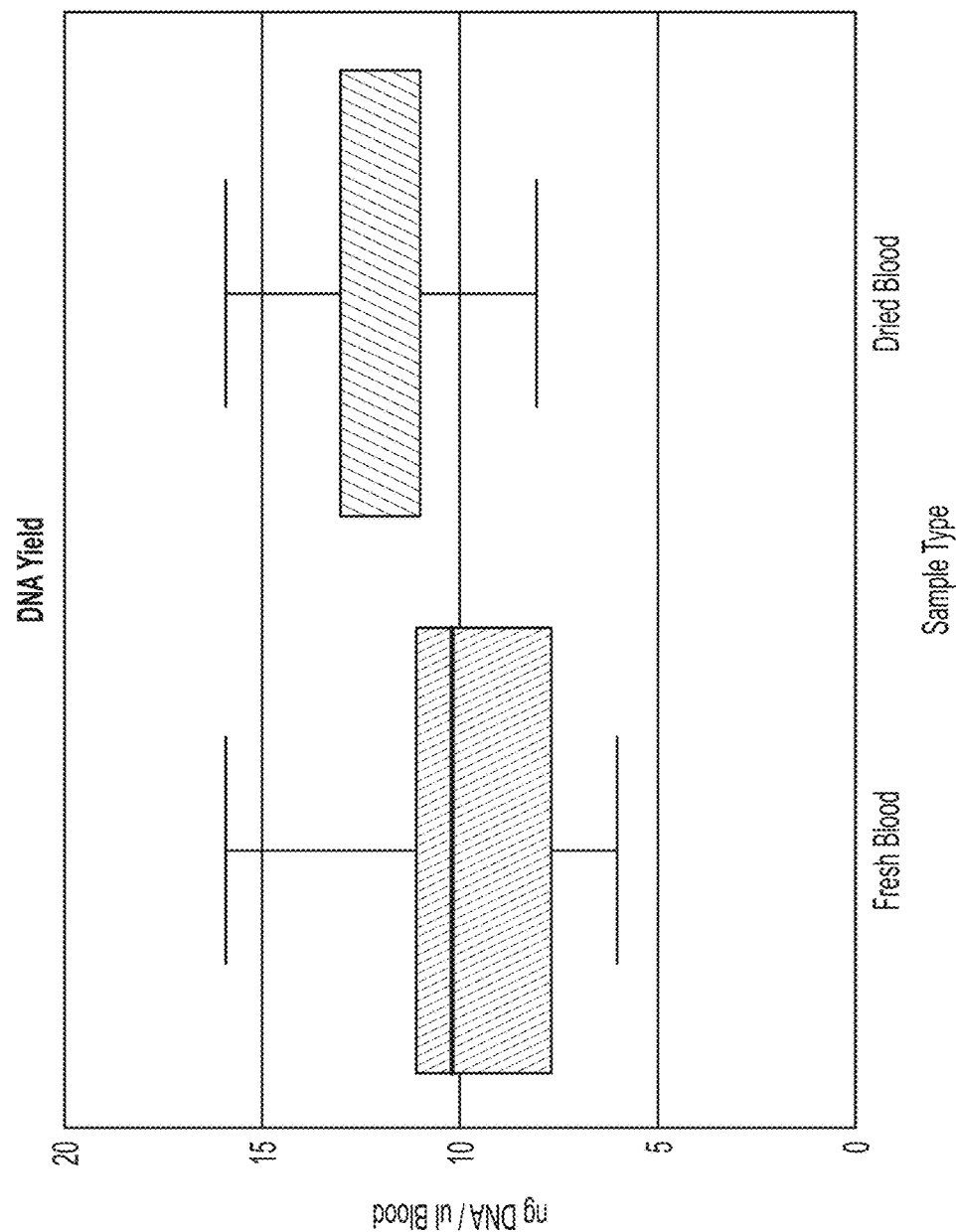
FIG. 19 shows DNA yield in experiments comparing performance of dried blood samples formed using a sample holder in an illustrative embodiment and fresh blood.
Figure 20:
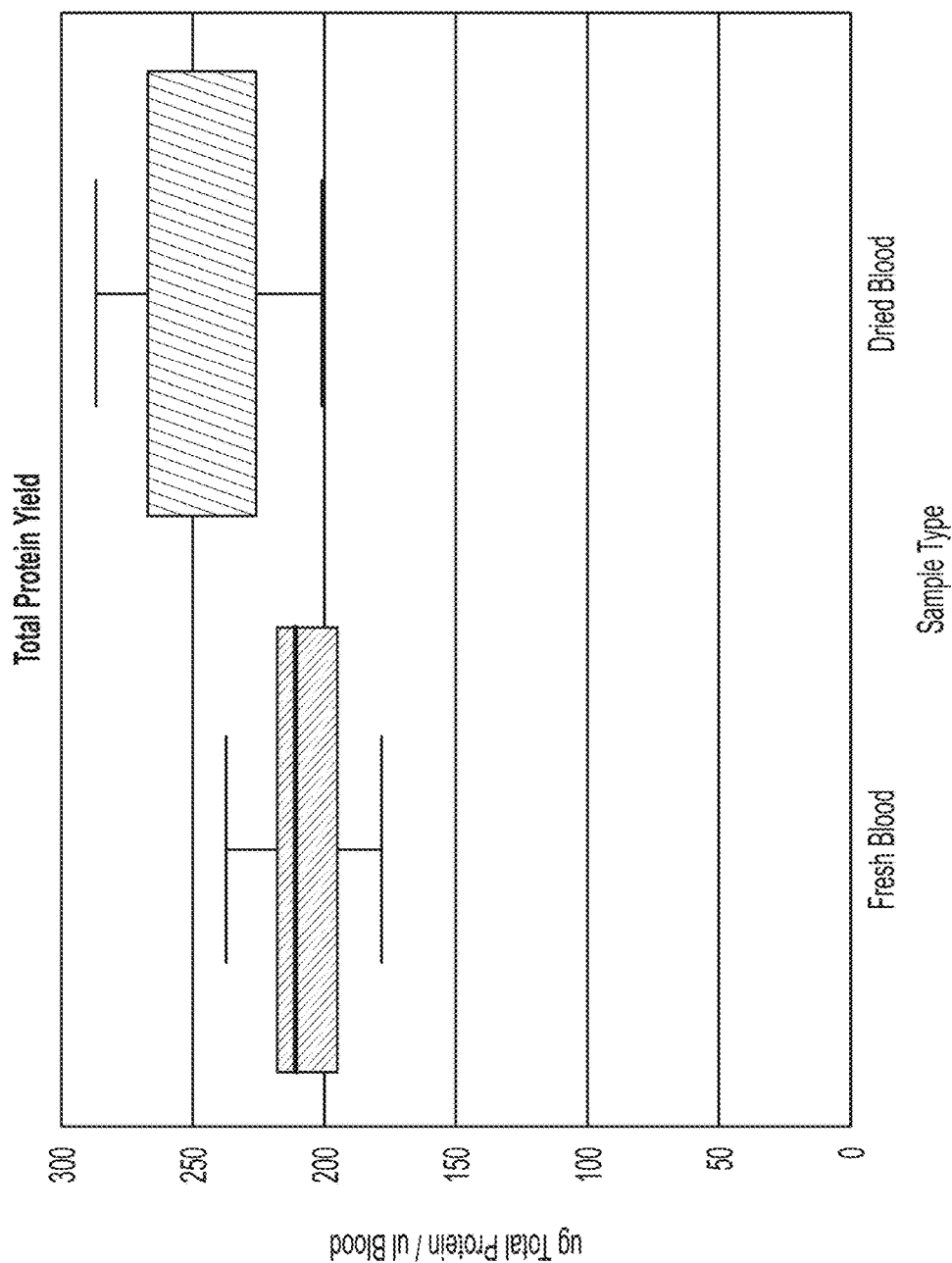
FIG. 20 shows the protein yield from comparing performance of dried blood samples formed using a sample holder in an illustrative embodiment and fresh blood.
Figure 21:
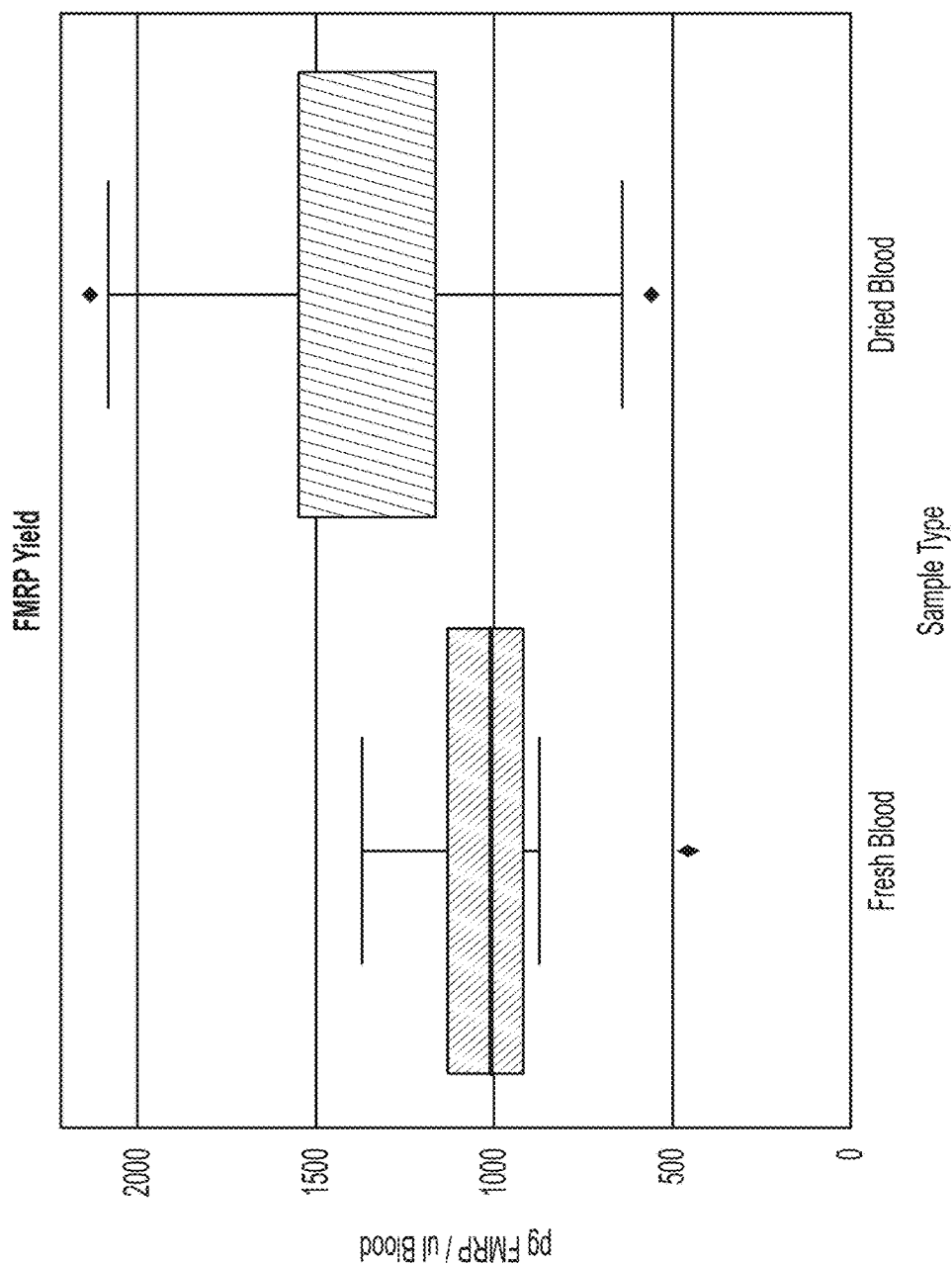
FIG. 21 illustrates the FMRP yield comparing performance of dried blood samples formed using a sample holder in an illustrative embodiment and fresh blood.

FIG. 19 shows the DNA yield from these experiments, and illustrates that the DNA yield from the dried blood samples is equal to, or greater than, that recovered from fresh blood. FIG. 20 shows the protein yield from these experiments, and again illustrates that the yield from the dried blood samples is equal to, or greater than, that recovered from fresh blood. FIG. 21 illustrates the FMRP yield, and again yield from the dried blood samples is equal to, or greater than, that recovered from fresh blood.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the present disclosure have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the present disclosure.

What is claimed is:

1. A sample holder, comprising:
a cap arranged to engage with and close an opening of at least one vessel, the cap having a top and a bottom, and a gripping surface between the top and bottom;
a porous element attached to the bottom of the cap and extending away from the bottom of the cap, the porous element arranged to absorb a blood sample including blood serum and other blood-borne materials having a size smaller than a threshold by wicking the blood serum into the porous element; and
a blotter element attached to the porous element and arranged to contact blood and wick blood serum and other blood-borne materials having a size smaller than the threshold to the porous element, the blotter element arranged to retain whole blood cells and other blood-borne materials having a size greater than the threshold in the blotter element such that the porous element absorbs only blood serum including any other blood-borne materials having a size smaller than the threshold.

2. The sample holder of claim 1, wherein the blotter element is separable from the porous element.

3. The sample holder of claim 1, wherein the blotter element is arranged to absorb up to 20 microliters of blood.

4. The sample holder of claim 1, further comprising a container having an internal space constructed and arranged to receive the cap, porous element and blotter element into the internal space, the container including a cover arranged to enclose the cap, porous element and blotter element in the internal space.

5. The sample holder of claim 4, wherein the internal space of the container is constructed and arranged to dry a blood sample held by the porous element and the blotter element with the porous element and the blotter element enclosed in the internal space.

6. The sample holder of claim 1, wherein the cap includes an identifying indicia that is inseparable from the cap and is attached to the cap prior to a blood sample being held by the porous element and the blotter element.

7. The sample holder of claim 6, wherein the cap includes an engagement feature to engage with a first vessel.

8. The sample holder of claim 7, further comprising the first vessel arranged to receive the porous element and the blotter element in a volume of the first vessel and to engage with the engagement feature of the cap to seal the porous element and the blotter element in the volume.

9. The sample holder of claim 8, wherein the first vessel is arranged to hold the porous element and the blotter element and a sample liquid during acoustic energy treatment of a blood sample held by the porous element and the blotter element employed to recover biomolecules in the blood sample.

10. The sample holder of claim 4, wherein the container includes a desiccant to receive moisture from blood in the porous element and the blotter element to dry the blood.

11. The sample holder of claim 10, wherein the container is arranged to hold a plurality of cap and porous element and blotter element assemblies.

12. The sample holder of claim 10, wherein the container and cover are arranged to enclose the cap, porous element and blotter element having an undried blood sample in a sealed space such that the desiccant receives moisture to dry the blood sample.

13. The sample holder of claim 1, wherein the porous element has a rod shape and is formed as a porous polymer fiber.

* * * * *